(12) United States Patent
Greisman et al.

(10) Patent No.: US 6,410,248 B1
(45) Date of Patent: Jun. 25, 2002

(54) GENERAL STRATEGY FOR SELECTING HIGH-AFFINITY ZINC FINGER PROTEINS FOR DIVERSE DNA TARGET SITES

(75) Inventors: Harvey A. Greisman, Brookline; Carl O. Pabo, Newton, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/240,179

(22) Filed: Jan. 29, 1999

Related U.S. Application Data

(60) Provisional application No. 60/073,223, filed on Jan. 30, 1998.

(51) Int. Cl.[7] .............................. G01N 33/50; C12Q 1/02
(52) U.S. Cl. .............................. 435/7.2; 435/4; 435/5; 435/6; 435/69.1; 435/DIG. 2; 435/DIG. 3; 435/DIG. 4; 435/DIG. 14; 435/DIG. 15; 436/501
(58) Field of Search ....................... 435/7.2, 6, 4, 5, 435/DIG. 4, DIG. 3, DIG. 2, DIG. 15, DIG. 14, 69.1; 436/501

(56) References Cited

U.S. PATENT DOCUMENTS

| | | | |
|---|---|---|---|
| 4,990,607 A | 2/1991 | Katagiri et al. | |
| 5,096,814 A | 3/1992 | Aivasidis et al. | |
| 5,096,815 A | 3/1992 | Ladner et al. | |
| 5,198,346 A | 3/1993 | Ladner et al. | |
| 5,223,409 A | 6/1993 | Ladner et al. | |
| 5,243,041 A | 9/1993 | Fernandez-Pol | |
| 5,302,519 A | 4/1994 | Blackwood et al. | |
| 5,324,638 A | 6/1994 | Tao et al. | |
| 5,324,818 A | 6/1994 | Nabel et al. | 530/350 |
| 5,324,819 A | 6/1994 | Oppermann et al. | |
| 5,340,739 A | 8/1994 | Stevens et al. | |
| 5,348,864 A | 9/1994 | Barbacid | |
| 5,350,840 A | 9/1994 | Call et al. | 536/23.1 |
| 5,356,802 A | 10/1994 | Chandrasegaran | 435/199 |
| 5,376,530 A | 12/1994 | De The et al. | 435/6 |
| 5,403,484 A | 4/1995 | Ladner et al. | |
| 5,436,150 A | 7/1995 | Chandrasegaran | 435/199 |
| 5,487,994 A | 1/1996 | Chandrasegaran | 435/199 |
| 5,498,530 A | 3/1996 | Schatz et al. | 435/6 |
| 5,578,483 A | 11/1996 | Evans et al. | 435/240.2 |
| 5,597,693 A | 1/1997 | Evans et al. | 435/6 |
| 5,639,592 A | 6/1997 | Evans et al. | 435/4 |
| 5,674,738 A | 10/1997 | Abramson et al. | 435/252.3 |
| 5,702,914 A | 12/1997 | Evans et al. | 435/7.1 |
| 5,789,538 A | 8/1998 | Rebar et al. | 530/324 |
| 5,792,640 A | 8/1998 | Chandrasegaran | 435/199 |
| 5,869,618 A | 2/1999 | Lippman et al. | 530/387 |
| 5,871,902 A | 2/1999 | Weininger et al. | |
| 5,871,907 A | * 2/1999 | Winter et al. | 435/6 |
| 5,916,794 A | 6/1999 | Chandrasegaran | 435/199 |
| 5,939,538 A | 8/1999 | Leavitt et al. | 536/23.1 |
| 5,972,615 A | 10/1999 | An et al. | 435/6 |
| 6,001,885 A | 12/1999 | Vega et al. | 514/725 |
| 6,007,988 A | 12/1999 | Choo et al. | 435/6 |
| 6,013,453 A | 1/2000 | Choo et al. | 435/6 |

FOREIGN PATENT DOCUMENTS

| | | |
|---|---|---|
| WO | WO 95/19431 | 7/1995 |
| WO | WO 96/06110 | 2/1996 |
| WO | WO 96/06166 | 2/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |

OTHER PUBLICATIONS

Agarwal et al., "Stimulation of Transcript Elongation Requires both the Zinc Finger and RNA Polymerase II Binding Domains of Human TFIIS," *Biochemistry*, 30(31):7842–7851 (1991).

Antao et al., "A thermodynamic study of unusually stable RNA and DNA hairpins," *Nuc. Acids. Res.*, 19(21):5901–5905 (1991).

Barbas, C. F., "Recent advances in phage display," *Curr. Opin. Biotech.*, 4:526–530 (1993).

Barbas et al., "Assembly of combinatorial antibody libraries on phage surfaces: The gene III site," *PNAS*, 88:7978–7982 (1991).

Barbas et al., "Semisynthetic combinatorial antibody libraries: A chemical solution to the diversity problem," *PNAS*, 89:4457–4461 (1992).

Beerli et al., "Toward controlling gene expression at will: Specific regulation of the erbB–2/HER–2 promoter by using polydactyl zinc finger proteins constructed from modular building blocks," *PNAS*, 95:14628–14633 (1998).

Bellefroid et al., "Clustered organization of homologous KRAB zinc–finger genes with enhanced expression in human T lymphoid cells," *EMBO J.*, 12(4):1363–1374 (1993).

Berg, J. M., "DNA Binding Specificity of Steriod Receptors," *Cell*, 57:1065–1068 (1989).

(List continued on next page.)

*Primary Examiner*—Bennett Celsa
(74) *Attorney, Agent, or Firm*—Robins & Pasternak LLP; Sean M. Brennan

(57) ABSTRACT

The present invention provides methods for making zinc finger proteins with high affinity for their targets, by sequentially selecting each finger of the protein.

15 Claims, 5 Drawing Sheets

(1 of 5 Drawing Sheet(s) Filed in Color)

OTHER PUBLICATIONS

Berg, J. M., "Sp1 and the subfamily of zinc finger proteins with guanine–rich binding sites," *PNAS*, 89:11109–11110 (1992).

Berg et al., "The Galvanization of Biology: A Growing Appreciation for the Roles of Zinc," *Science*, 271:1081–1085 (1996).

Berg, J.M., "Letting your fingers do the walking," *Nature Biotechnology*, 15:323 (1997).

Bergqvist et al., "Loss of DNA–binding and new transcriptional trans–activation function in polyomavirus large T–antigen with mutation of zinc finger motif," *Nuc. Acids Res.*, 18(9):2715–2720 (1990).

Blaese et al., "Vectors in cancer therapy: how will they deliver?," *Cancer Gene Therapy*, 2(4):291–297 (1995).

Caponigro et al., "Transdominant genetic analysis of a growth control pathway," *PNAS*, 95:7508–7513 (1998).

Celenza et al., "A Yeast Gene That Is Essential for Release from Glucose Repression Encodes a Protein Kinase," *Science*, 233:1175–1180 (1986).

Cheng et al., "Identification of Potential Target Genes for Adr1p through Characterization of Essential Nucleotides in UAS1," *Mol. Cellular Biol.*, 14(6):3842–3852 (1994).

Choo et al., "A role in DNA binding for the linker sequences of the first three zinc fingers of TFIIIA," *Nuc. Acids Res.*, 21(15):3341–3346 (1993).

Choo et al., "Designing DNA–binding proteins on the surface of filamentous phage," *Curr. Opin. Biotechnology*, 6:431–436 (1995).

Choo et al., "Promoter–specific Activation of Gene Expression Directed by Bacteriophage–selected Zinc Fingers," *J. Mol. Biol.*, 273:525–532 (1997).

Choo, Y., "Recognition of DNA methylation by zinc fingers," *Nature Struct. Biol.*, 5(4):264–265 (1998).

Choo et al., "All wrapped up," *Nature Structural Biology*, 5(4):253–255 (1998).

Choo, Y., "End effects in DNA recognition by zinc finger arrays," *Nuc. Acids Res.*, 26(2):554–557 (1998).

Choo et al., "Physical basis of a protein–DNA recognition code," *Curr. Opin. Struct. Biol.*, 7(1):117–125 (1997).

Clarke et al., "Zinc Fingers in *Caenorhabditis elegans*: Finding Families and Probing Pathways," *Science*, 282:2018–2022 (1998).

Crozatier et al., "Single Amino Acid Exchanges in Separate Domains of the Drosophila serendipity δ Zinc Finger Protein Cause Embryonic and Sex Biased Lethality," *Genetics*, 131:905–916 (1992).

Debs et al., "Regulation of Gene Expression in Vivo by Liposome–mediated Delivery of a Purified Transcription Factor*," *J. Biological Chemistry*, 265(18):10189–10192 (1990).

Desjarlais et al., "Redesigning the DNA–Binding Specificity of a Zinc Finger Protein: A Data Base–Guided Approach," *Proteins: Structure, Function, and Genetics*, 13(3):272 (1992).

DiBello et al., "The Drosophila Broad–ComplexEncodes a Family of Related Proteins Containing Zinc Fingers," *Genetics*, 129:385–397 (1991).

Elrod–Erickson et al., "High–resolution structures of variant Zif268–DNA complexes: implications for understanding zinc finger–DNA recognition," *Structure*, 6(4):451–464 (1998).

Elrod–Erickson et al., "Zif268 protein–DNA complex refined at 1.6 Å: a model system for understanding zinc finger–DNA interactions," *Structure*, 4(10):1171–1180 (1996).

Fairall et al., "The crystal structure of a two zinc–finger peptide reveals an extension to the rules for zinc–finger/DNA recognition," *Nature*, 366:483–487 (1993).

Frankel et al., "Fingering Too Many Proteins," *Cell*, 53:675 (1988).

Friesen et al., "Phage Display of RNA Binding Zinc Fingers from Transcription Factor IIIA*," *J. Biological Chem.*, 272(17):10994–10997 (1997).

Friesen et al., "Specific RNA binding proteins constructed from zinc fingers," *Nature Structural Biology*, 5(7):543–546 (1998).

Gogos et al., "Recognition of diverse sequences by class I zinc fingers: Asymmetries and indirect effects on specificity in the interaction between CF2II and A+T–rich sequence elements," *PNAS*, 93(5):2159–2164 (1996).

Gossen et al., "Tight control of gene expression in mammalian cells by tetracycline–responsive promoters," *PNAS*, 89:5547–5551 (1992).

Hamilton et al., "High affinity binding sites for the Wilms' tumor suppressor protein WT1," *Nuc. Acids Res.*, 23(2):277–284 (1995).

Hanas et al., "Internal deletion mutants of Xenopus transcription factor IIIA," *Nuc. Acids Res.*, 17(23):9861–9870 (1989).

Hayes et al., "Locations of Contacts between Individual Zinc Fingers of *Xenopus laevis* Transcription Factor IIIA and the Internal Control Region of a 5S RNA Gene," *Biochemistry*, 31:11600–11605 (1992).

Heinzel et al., "A complex containing N–CoR, mSin3 and histone deacetylase mediates transcriptional repression," *Nature*, 387:43–48 (1997).

Hirst et al., "Discrimination of DNA response elements for thyroid hormone and estrogen is dependant on dimerization of receptor DNA binding domains," *PNAS*, 89:5527–5531 (1992).

Hoffman et al., "Structures of DNA–binding mutant zinc finger domains: Implications for DNA binding," *Protein Science*, 2:951–965 (1993).

Isalan et al., "Synergy between adjacent zinc fingers in sequence–specific DNA recognition," *PNAS*, 94(11):5617–5621 (1997).

Isalan et al., "Comprehensive DNA Recognition through Concerted Interactions from Adjacent Zinc Fingers," *Biochemistry*, 37:12026–12033 (1998).

Jacobs, G. H., "Determination of the base recognition positions of zinc fingers from sequence analysis," *EMBO J.*, 11(12):4507–4517 (1992).

Jamieson et al., "A zinc finger directory for high–affinity DNA recognition," *PNAS*, 93:12834–12839 (1996).

Julian et al., "Replacement of His23 by Cys in a zinc finger of HIV–1 NCp7 led to a change in 1H NMR–derived 3D structure and to a loss of biological activity," *FEBS letters*, 331(1,2):43–48 (1993).

Kamiuchi et al., "New multi zinc finger protein: biosynthetic design and characteristics of DNA recognition," *Nucleic Acids Symposium Series*, 37:153–154 (1997).

Kim et al., "Serine at Position 2 in the DNA Recognition helix of a Cys2–His2 Zinc finger Peptide is Not, in General, Responsible for Base Recognition," *J. Mol. Biol.*, 252:1–5 (1995).

Kim et al., "Site–specific cleavage of DNA–RNA hybrids by zinc finger/FokI cleavage domain fusions," *Gene*, 203:43–49 (1997).

Kim et al., "A 2.2 A° resolution crystal structure of a designed zinc finger protein bound to DNA," *Nat. Struct. Biol.*, 3(11):940–945 (1996).

Kim et al., "Getting a handhold on DNA: Design of poly–zinc finger proteins with femtomolar dissociation constants," *PNAS*, 95:2812–2817 (1998).

Kim et al., "Design of TATA box–binding protein/zinc finger fusions for targeted regulation of gene expression," *PNAS*, 94:3616–3620 (1997).

Kim et al., "Hybrid restriction enzymes: Zinc finger fusions to Fok I cleavage domain," *PNAS*, 93:1156–1160 (1996).

Kim et al., "Transcriptional repression by zinc finger peptides," *J. Biol. Chem.*, 272(47):29795–28000 (1997).

Kinzler et al., "The GLI gene is a member of the Kruppel family of zinc finger proteins," *Nature*, 332:371–4 (1988).

Klug, A., "Gene Regulatory Proteins and Their Interaction with DNA," *Ann. NY Acad. Sci.*, 758:143–160 (1995).

Klug et al., "Protein Motifs 5: Zinc Fingers," *FASEB J.*, 9:597–604 (1995).

Kulda et al., "The regulatory gene areA mediating nitrogen metabolite repression in *Aspergillus nidulans*. Mutations affecting specificity of gene activation alter a loop residue of a putative zinc finger," *EMBO J.*, 9(5):1355–1364 (1990).

Laird–Offringa et al., "RNA–binding proteins tamed," *Nat. Structural Biol.*, 5(8):665–668 (1998).

Mandel–Gutfreund et al., "Quantitative parameters for amino acid–base interaction: implications for prediction of protein–DNA binding sites," *Nuc. Acids Res.*, 26(10):2306–2312 (1998).

Margolin et al., "Kruppel–associated boxes are potent transcriptional repression domains," *PNAS*, 91:4509–4513 (1994).

Mizushima et al., "pEF–BOS, a powerful mammilian expression vector," *Nuc. Acids Res.*, 18(17):5322 (1990).

Nardelli et al., "Base sequence discrimination by zinc–finger DNA–binding domains," *Nature*, 349:175–178 (1991).

Nekludova et al., "Distinctive DNA conformation with enlarged major groove is found in Zn–finger—DNA and other protein—DNA complexes," *PNAS*, 91:6948–6952 (1994).

Orkin et al., "Report and Recommendations of the Panel to Assess the NIH Investment in Research on Gene Therapy" (1995).

Pabo et al., "Systematic Analysis of Possible Hydrogen Bonds between Amino Acid Side Chains and B–form DNA," *J. Biomolecular Struct. Dynamics*, 1:1039–1049 (1983).

Pabo et al., "Protein–DNA Recognition," *Ann. Rev. Biochem.*, 53:293–321 (1984).

Pabo, C. O., "Transcription Factors: Structural Families and Principals of DNA Recognition," *Ann. Rev. Biochem.*, 61:1053–1095 (1992).

Pavletich et al., "Crystal Structure of a Five–Finger GLI–DNA Complex: New Perspectives on Zinc Fingers," *Science*, 261:1701–1707 (1993).

Pavletich et al., "Zinc Finger–DNA Recognition: Crystal Structure of a Zif268–DNA Complex at 2.1 Å," *Science*, 252:809–817 (1991).

Pengue et al., "Repression of transcriptional activity at a distance by the evolutionarily conserved KRAB domain present in a subfamily of zinc finger proteins," *Nuc. Acids Res.*, 22(15):2908–2914 (1994).

Pengue et al., "Transcriptional Silencing of Human Immunodeficiency Virus Type 1 Long Terminal Repeat–Driven Gene Expression by the Kruppel–Associated Box Repressor Domain Targeted to the Transactivating Response Element," *J. Virology*, 69(10):6577–6580 (1995).

Pengue et al., "Kruppel–associated box–mediated repression of RNA polymerase II promoters is influenced by the arrangement of basal promoter elements," *PNAS*, 93:1015–1020 (1996).

Pomerantz et al., "Structure–Based Design of a Dimeric Zinc Finger Protein," *Biochemistry*, 37(4):965–970 (1998).

Qian et al., "Two–Dimensional NMR Studies of the Zinc Finger Motif: Solution Structures and Dynamics of Mutant ZFY Domains Containing Aromatic Substitutions in the Hydrophobic Core," *Biochemistry*, 31:7463–7476 (1992).

Quigley et al., "Complete Androgen Insensitivity Due to Deletion of Exon C of the Androgen Receptor Gene Highlights the Functional Importance of the Second Zinc Finger of the Androgen Receptor in Vivo," *Molecular Endocrinology*, 6(7):1103–1112 (1992).

Rauscher et al., "Binding of the Wilms' Tumor Locus Zinc Finger Protein to the EGR–1 Consensus Sequence," *Science*, 250:1259–1262 (1990).

Ray et al., "Repressor to activator switch by mutations in the first Zn finger of the glucocorticoid receptor: Is direct DNA binding necessary?," *PNAS*, 88:7086–7090 (1991).

Rebar et al., "Phage Display Methods for Selecting Zinc Finger Proteins with Novel DNA–Binding Specificities," *Methods in Enzymology*, 267:129–149 (1996).

Reith et al., "Cloning of the major histocompatibility complex class II promoter binding protein affected in a hereditary defect in class II gene regulation," *PNAS*, 86:4200–4204 (1989).

Rhodes et al., "Zinc Fingers: They play a key part in regulating the activity of genes in many species, from yeast to humans. Fewer than 10 years ago no one knew they existed," *Scientific American*, 268:56–65 (1993).

Rice et al., "Inhibitors of HIV Nucleocapsid Protein Zinc Fingers as Candidates for the Treatment of AIDS," *Science*, 270:1194–1197 (1995).

Rivera et al., "A humanized system for pharmacologic control of gene expression," *Nature Medicine*, 2(9):1028–1032 (1996).

Rollins et al., "Role of TFIIIA Zinc Fingers In vivo: Analysis of Single–Finger Function in Developing Xenopus Embryos," *Molecular Cellular Biology*, 13(8):4776–4783 (1993).

Saleh et al., "A Novel Zinc Finger Gene on Human Chromosome 1qter That Is Alternatively Spliced in Human Tissues and Cell Lines," *Am. J. Hum. Genet.*, 52:192–203 (1993).

Shi et al., "Specific DNA–RNA Hybrid Binding by Zinc Finger Proteins," *Science*, 268:282–284 (1995).

Shi et al., "DNA Unwinding Induced by Zinc Finger Protein Binding," *Biochemistry*, 35:3845–3848 (1996).

Shi et al., "A direct comparison of the properties of natural and designed finger proteins," *Chem. & Biol.*, 2(2):83–89 (1995).

Singh et al., "Molecular Cloning of an Enhancer Binding Protein: Isolation by Screening of an Expression Library with a Recognition Site DNA," *Cell,* 52:415–423 (1988).

South et al., "The Nucleocapsid Protein Isolated from HIV–1 Particles Binds Zinc and Forms Retroviral–Type Zinc Fingers," *Biochemistry,* 29:7786–7789 (1990).

Suzuki et al., "Stereochemical basis of DNA recognition by Zn fingers," *Nuc. Acids Res.,* 22(16):3397–3405 (1994).

Suzuki et al. "DNA recognition code of transcription factors in the helix–turn–helix, probe helix, hormone receptor, and zinc finger families," *PNAS,* 91:12357–12361 (1994).

Swirnoff et al., "DNA–Binding Specificity of NGFI–A and Related Zinc Finger Transcription Factors," *Mol. Cell. Biol.,* 15(4):2275–2287 (1995).

Thiesen et al., "Determination of DNA binding specificities of mutated zinc finger domains," *FEBS Letters,* 283(1):23–26 (1991).

Thiesen et al., "Amino Acid Substitutions in the SP1 Zinc Finger Domain Alter the DNA Binding Affinity to Cognate SP1 Target Site," *Biochem. Biophys. Res. Communications,* 175(1):333–338 (1991).

Thukral et al., "Localization of a Minimal Binding Domain and Activation Regions in Yeast Regulatory Protein ADR1," *Molecular Cellular Biology,* 9(6):2360–2369 (1989).

Thukral et al., "Two Monomers of Yeast Transcription Factor ADR1 Bind a Palindromic Sequence Symmetrically to Activate ADH2 Expression," *Molecular Cellular Biol.,* 11(3):1566–1577 (1991).

Thukral et al., "Alanine scanning site–directed mutagenesis of the zinc fingers of transcription factor ADR1: Residues that contact DNA and that transactivate," *PNAS,* 88:9188–9192 (1991), + correction page.

Vortkamp et al., "Identification of Optimized Target Sequences for the GLI3 Zinc Finger Protein," *DNA Cell Biol.,* 14(7):629–634 (1995).

Webster et al., "Conversion of the E1A Cys4 zinc finger to a nonfunctional His2, Cys2 zinc finger by a single point mutation," *PNAS,* 88:9989–9993 (1991).

Whyatt et al., "The two zinc finger–like domains of GATA–1 have different DNA binding specificities," *EMBO J.,* 12(13):4993–5005 (1993).

Wilson et al., "In Vivo Mutational analysis of the NGFI–A Zinc Fingers*," *J. Biol. Chem.,* 267(6):3718–3724 (92).

Witzgall et al., "The Kruppel–associated box–A (KRAB–A) domain of zinc finger proteins mediates transcriptional repression," *PNAS,* 91:4514–4518 (1994).

Wright et al., "Expression of a Zinc Finger Gene in HTLV–I– and HTLV–II–transformed Cells," *Science,* 248:588–591 (1990).

Yang et al., "Surface plasmon resonance based kinetic studies of zinc finger–DNA interactions," *J. Immunol. Methods,* 183:175–182 (1995).

Yu et al., "A hairpin ribozyme inhibits expression of diverse strains of human immunodeficiency virus type 1," *PNAS,* 90:6340–6344 (1993).

Desjarlais and Berg, Redesigning the DNA–Binding Specificity of a Zinc Finger Protein: A Data Base–Guided Approach, Proteins: *Structure, Function, and Genetics* 12:101–104 (1992).

Thukral et al., Mutations in the Zinc Fingers of ADR1 That Change theSpecificity of DNA Binding and Transactivation, *Molecular and Cellular Biology,* p. 2784–2792 (6/92).

Nardelli et al., Zinc finger–DNA recognition: analysis of base specificity by Site–directed mutagenesis, *Nucleic Acids research,* 20:(16) 4137–4144 (1992).

Cheng and Young, A Single Amino Acid substitution in Zinc Finger 2 of Adrlp Changes its Binding Specificity at two Positions in UAS1, *J. Mol. Biol.,* 251:1–8 (1995).

Taylor et al., Designing Zinc–Finer ADR1 Mutants with Altered Specificity of DNA Binding to T in UAS1 Sequences, *Biochemistry,* 34:3222–3230 (1995).

Pomerantz et al., Analysis of homeodomain function by structure–based design of a transcription factor, *Proc. Natl. Acad. Sci,* 92:9752–9756 (10/95).

Desjarlais and Berg, Length–encoded multiplex binding site determination: Application to zinc finger proteins, *Natl. Acad. Sci,* 91:1099–11103 (11/94).

Desjarlais and Berg, Use of a zinc–finger consensus sequence framework and specificity rules to design specific DNA binding proteins, *Proc. Natl. Acad. Sci,* 90:2256–2260 (3/93).

Choo et al., In vivo repression by a site–specific DNA binding protein designed against an oncogenic sequence, *Nature,* 372:642–645 (Dec. 15, 1994).

Greisman and Pabo, A General Strategy for Selecting High–Affinity Zinc Finger Proteins for Diverse DNA Target Sites, *Science,* 275:657–661 (Jan. 31, 1997).

Pomerantz et al., Structure–Based Design of Transcription Factors, *Science,* 267:93–96 (Jan. 6, 1995).

Liu et al., Design of polydactyl zinc–finger proteins for unique addressing within complex genomes, *Proc. Natl. Acad. Sci.,* 94:5525–5530 (5/97).

Choo and Klug, Selection of DNA binding sites for zinc fingers using rationally randomized DNA reveals coded interactions, *Proc. Natl. Acad. Sci,* 91:11168–11172 (11/94).

Desjarlais and Berg, Toward rules relating zinc finger protein sequences and DNA binding site preferences, *Proc. Natl. Acad.,* 89:7345–7349 (8/92).

Choo and Klug, Toward a code for the interactions of zinc fingers with DNA: Selection of randomized fingers displayed on phage, *Proc. natl. Acad. Sci.,* 91:11163–11167 (11/94).

Jamieson et al., In Vitro Selection of Zinc Fingers with Altered DNA–Binding Specificity, *Biochemistry,* 33:5689–5695 (1994).

Wu et al., Building zinc fingers by seletion: Toward a therapeutic application, *Proc. Natl. Acad. Sci,* 92:344–348 (1/95).

Rebar and Pabo, Zinc Finger Phage: Affinity Selection of Fingers with new DNA–Binding Specificities, *Science,* 263:671–673 (Feb. 4, 1994).

Corbi et al., "Synthesis of a New Zinc Finger Peptide; Comparison of Its 'Code' Deduced and 'CASTing' Derived Binding Sites," *FEBS Letters,* 417:71–74 (1997).

* cited by examiner

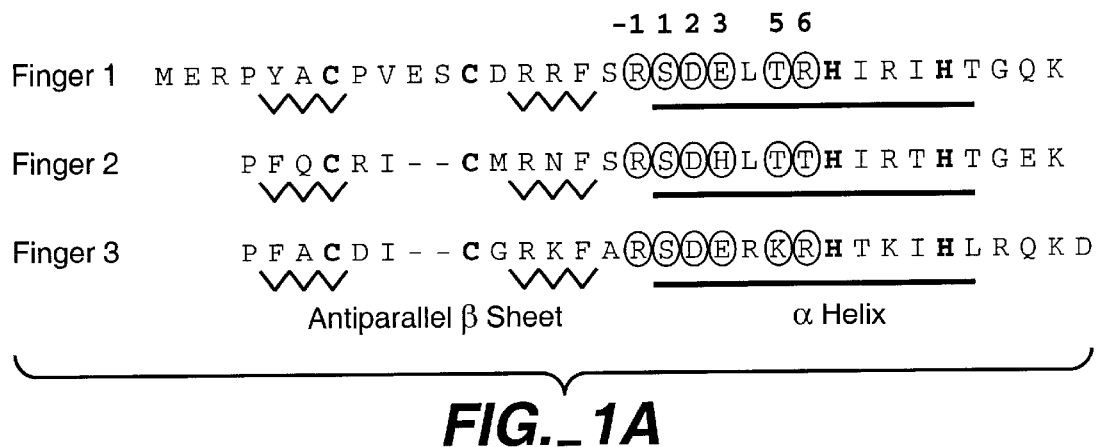
FIG._1A
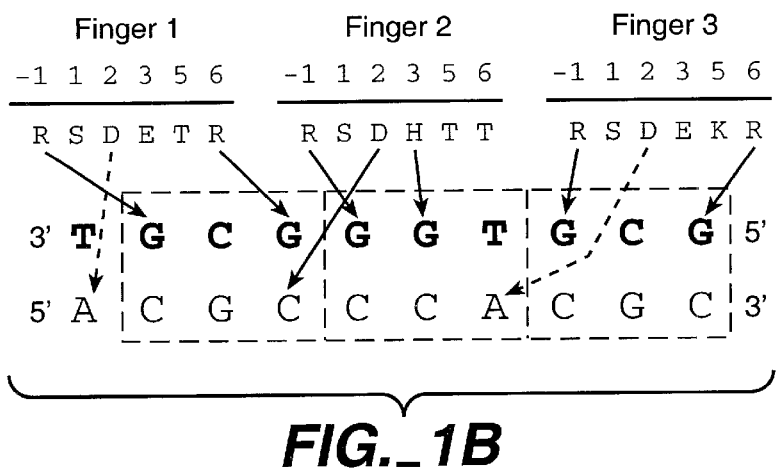
FIG._1B
```
TATA  3' G  A  A  A  A  T  A  T  C  G  G  5'
p53   3' T  T  G  T  A  C  A  G  G  G  T  5'
NRE   3' G  A  C  T  T  G  G  G  A  A  C  5'
```
FIG._1C

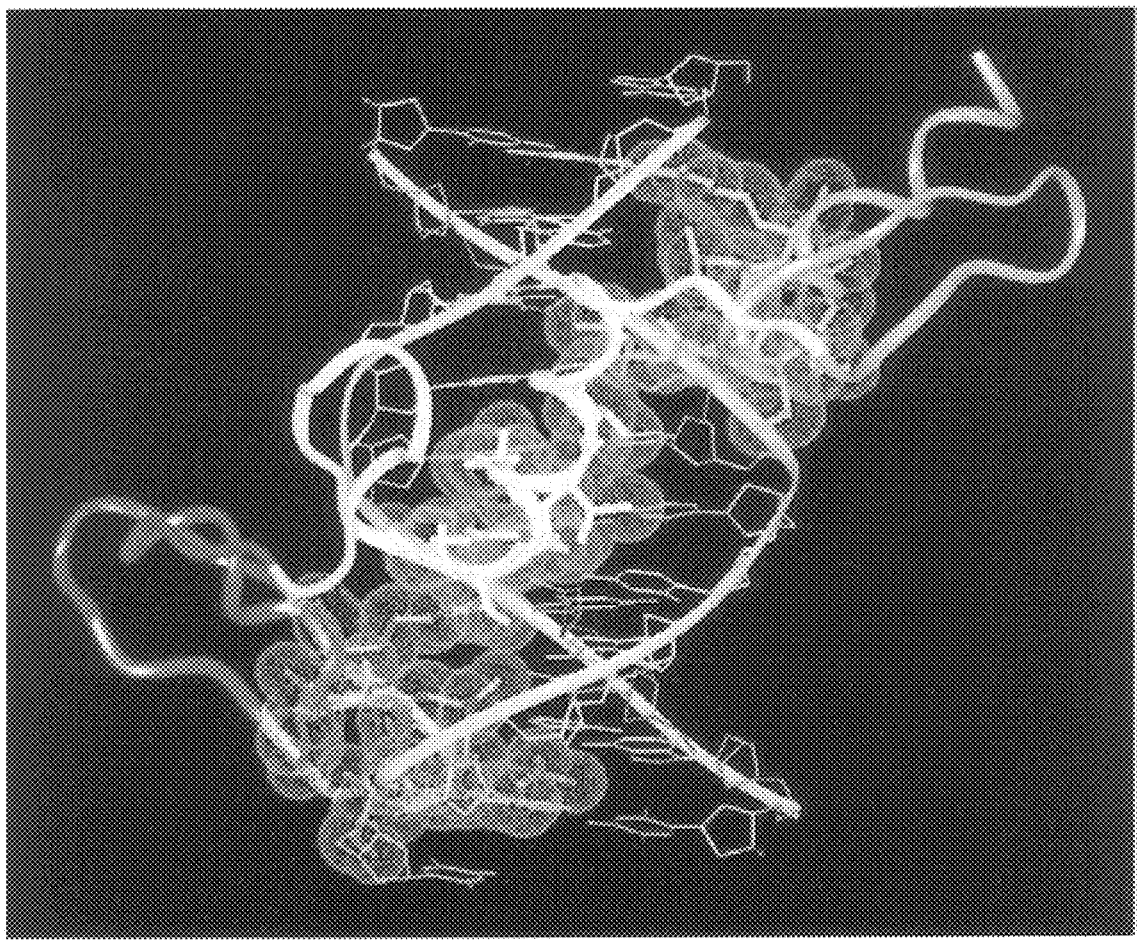
FIG._1D

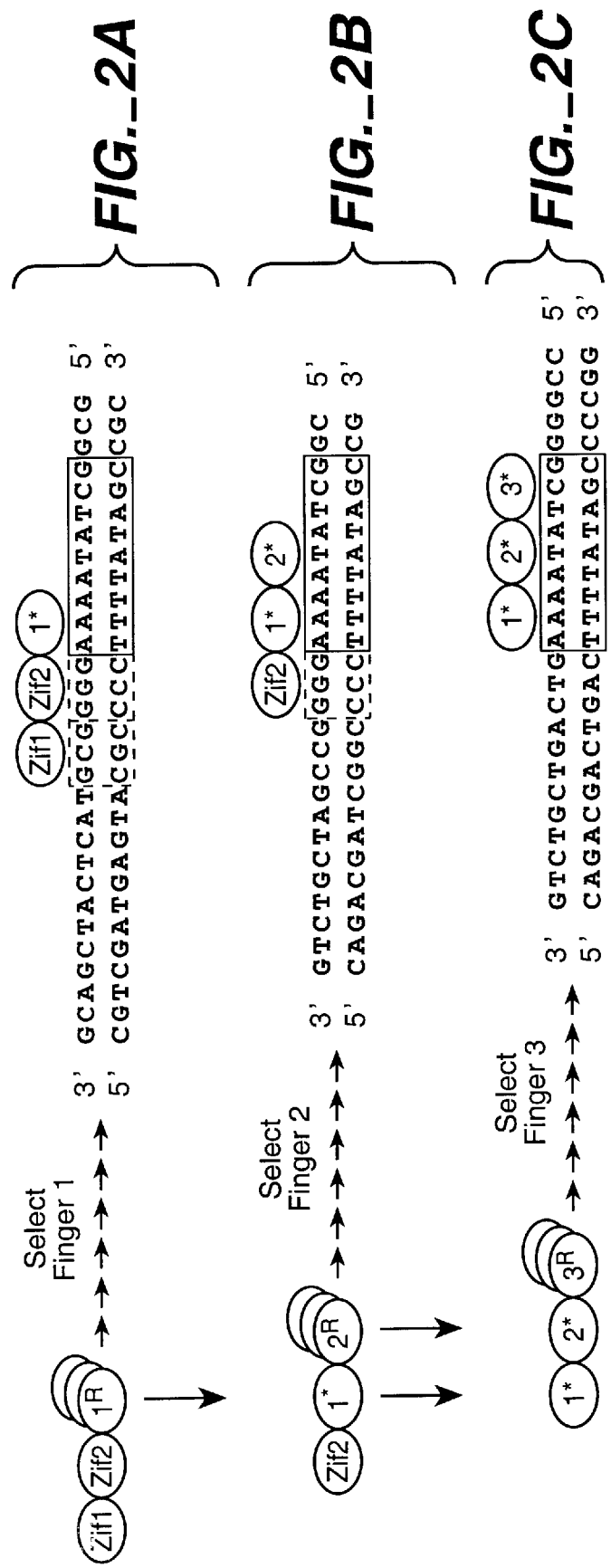
FIG._2A
FIG._2B
FIG._2C

TATA Box

| Finger 1 | Finger 2 | Finger 3 |
|---|---|---|
| -1 1 2 3 5 6 | -1 1 2 3 5 6 | -1 1 2 3 5 6 |
| Q K T N I T | Q Q T A N Q | T L Q T N R |
| Q K T N D T | Q H T G N Q | T L H T D R |
| Q K N N L A | Q L T G N Q | T L H T S R |
| Q K N N I N | Q R T G D Q | T H A T N R |
| Q K T N I T | Q Q T A N Q | T L G T D R |
| Q K T N D T | Q Q A S N A | T L H T T R |
| Q K T N D T | Q Q A S N A | T L H T T R |
| Q K T N I T | Q A A S Q A | T S G D G R |
| Q K t N i t | Q q t n q | T I h t R |

```
3' G  A A A  A T A  T C G  G 5'
5' C  T T T  T A T  A G C  C 3'
```

FIG._3A p53 Binding Site

| Finger 1 | Finger 2 | Finger 3 |
|---|---|---|
| -1 1 2 3 5 6 | -1 1 2 3 5 6 | -1 1 2 3 5 6 |
| M S H H K E | Q R G T T R | R L H H L L |
| M S H H K E | Q Q G T N R | R L H H T L |
| M S H H K E | Q R G T T R | R L H H L A |
| M S H H K E | Q R G T T R | R H H H L V |
| M S H H K E | Q Q G T N R | R L H H V L |
| M S H H K E | Q Q G T N R | R L H H V L |
| M S H H K E | Q Q G T N R | R L H H T L |
| M S H H K E | Q R G T T R | R L H H V V |
| M S H H K E | Q r/q G T t/n R | R I H H I |

Nuclear Receptor Element

| Finger 1 | | | | | | Finger 2 | | | | | | Finger 3 | | | | | |
|---|---|---|---|---|---|---|---|---|---|---|---|---|---|---|---|---|---|
| -1 | 1 | 2 | 3 | 5 | 6 | -1 | 1 | 2 | 3 | 5 | 6 | -1 | 1 | 2 | 3 | 5 | 6 |
| Q | S | H | D | T | K | D | S | S | H | A | R | R | L | D | G | T | A |
| Q | S | H | D | T | K | D | S | S | K | S | R | R | P | D | N | H | A |
| Q | S | H | D | T | K | D | S | S | H | A | R | R | L | D | N | T | V |
| Q | S | H | D | T | K | D | S | S | K | S | R | R | P | D | N | T | D |
| Q | S | H | D | T | K | D | S | S | K | S | R | R | P | D | Q | R | A |
| Q | S | H | D | T | K | D | S | S | K | S | R | R | Q | D | G | M | I |
| Q | S | H | D | T | K | D | S | S | K | S | R | R | K | D | Q | T | T |
| Q | S | H | D | T | K | D | S | S | K | S | R | R | L | D | N | T | A |
| Q | S | H | D | T | K | D | S | S | k | s | R | R |   | D | n | t | a |

GENERAL STRATEGY FOR SELECTING HIGH-AFFINITY ZINC FINGER PROTEINS FOR DIVERSE DNA TARGET SITES

CROSS-REFERENCES TO RELATED APPLICATIONS

This application claims priority from U.S. Ser. No. 60/073,223, filed Jan. 30, 1998, herein incorporated by reference in its entirety.

STATEMENT AS TO INVENTIONS MADE UNDER FEDERALLY SPONSORED RESEARCH AND DEVELOPMENT

Not applicable.

BACKGROUND OF THE INVENTION

Design of DNA binding proteins that will recognize desired target sites on double-stranded DNA presents a challenging situation. A number of DNA-binding motifs have yielded variants with altered specificities, and zinc finger proteins related to TFIIIA (Miller et al., *EMBO J.* 4:1609 (1985)) and Zif268 (Christy et al., *Proc. Natl. Acad. Sci. U.S.A.* 85:7857 (1988)) appear to provide a versatile framework for design. Modeling, sequence comparisons, and phage display have been used to alter the specificity of an individual zinc finger within a multifinger protein (Nardelli et al., *Nucleic Acids Res.* 20:4137 (1992); Thukral et al., *Mol. Cell. Biol.* 12:2784 (1992); Desjarlais et al., *Proteins* 12:101 (1992) Desjarlais et al., *Proteins* 13:272 (1992); *Proc. Natl. Acad. Sci. U.S.A.* 89:7345 (1992); *Proc. Natl. Acad. Sci. U.S.A.* 91:11099 (1994); Rebar et al., *Science* 263:671 (1994); Choo et al., *Proc. Natl. Acad. Sci. U.S.A.* 91:11163 (1994); Choo et al., *Proc. Natl. Acad. Sci. U.S.A.* 91:11168; Jamieson et al., *Biochemistry* 33:5689 (1994); Wu et al., *Proc Natl. Acad. Sci. U.S.A.* 92:344 (1995); Taylor et al., *Biochemistry* 34:3222 (1995); Cheng et al., *J. Mol. Biol.* 251:1 (1995)), and fingers also have been "mixed and matched" to construct new DNA binding proteins (Desjarlais et al., *Proc. Natl. Acad. Sci. U.S.A.* 90:2256 (1993); Choo et al., *Nature* 372:642 (1994)).

These design and selection studies have assumed that each finger (with a corresponding, 3 base pair (bp) subsite) can be treated as an independent unit (FIG. 1B). This assumption has provided a useful starting point for design studies, but crystallographic studies of zinc finger-DNA complexes reveal many examples of contacts that couple neighboring fingers and subsites (Pavletich et al., *Science* 252:809 (1991); Fairall et al., *Nature* 366:483 (1993); Pavletich et al., *Science* 261:1701 (1993); Elrod-Erickson et al., *Structure* 4:1171 (1996)). Context-dependent interactions are therefore important for zinc finger-DNA recognition (Nardelli et al., *Nucleic Acids Res.* 20:4137 (1992); Thukral et al., *Mol. Cell. Biol.* 12:2784 (1992); Desjarlais et al., *Proteins* 12:101 (1992); Desjarlais et al., *Proteins* 13:272 (1992); *Proc. Natl. Acad. Sci. U.S.A.* 89:7345 (1992); *Proc. Natl. Acad. Sci. U.S.A.* 91:11099 (1994); Taylor et al., *Biochemistry* 34:3222 (1995); Cheng et al., *J. Mol. Biol.* 251:1 (1995); Desjarlais et al., *Proc. Natl. Acad. Sci. U.S.A.* 90:2256 (1993)).

"Mix and match" design strategies have, so far, been limited to binding sites in which the primary strand (FIG. 1B) contains at least one guanine within each 3 bp subsite (Nardelli et al., *Nucleic Acids Res.* 20:4137 (1992); Thukral et al., *Mol. Cell. Biol.* 12:2784 (1992); Desjarlais et al., *Proteins* 12:101 (1992); Desjarlais et al., *Proteins* 13:272 (1992); *Proc. Natl. Acad. Sci. U.S.A.* 89:7345 (1992); *Proc. Natl. Acad. Sci. U.S.A.* 91:11099 (1994); Desjarlais et al., *Proc. Natl. Acad. Sci. U.S.A.* 90:2256 (1993); Choo et al., *Nature* 372:642 (1994)). The affinities of designed zinc finger proteins also have varied widely, and some $K_d$s have been in the micromolar range (Desjarlais et al., *Proc. Natl. Acad. Sci. U.S.A.* 90:2256 (1993); Choo et al, *Nature* 372:642 (1994)). Subtle, context-dependent interactions may have a critical cumulative effect when optimizing, multifinger proteins: A modest (10-fold) increase in affinity for each finger may yield a substantial (1000-fold) increase in affinity for a three-finger protein. However, existing strategies have not taken these context-dependent interactions into account when designing multi-finger zinc finger proteins that bind to a target site.

SUMMARY OF THE INVENTION

The present invention therefore provides a selection strategy for a making multi-finger zinc finger proteins that takes into account context-dependent interactions of zinc fingers and target subsites. This strategy thus provides a means for making zinc finger proteins that bind to a specific target site.

In one aspect, the present invention provides a method of making a zinc finger protein that binds to a target site, the method comprising the steps of: (i) providing a target site comprising first, second, and third subsites; (ii) identifying a first finger of the zinc finger protein by: (a) providing a nucleic acid library encoding variants of a zinc finger protein comprising a randomized first finger, and constant fingers that bind to known subsites; and (b) selecting a first zinc finger protein that binds to a target site comprising the first subsite and the known subsites, the first zinc finger protein comprising a selected variant first finger and the constant fingers; (iii) identifying a second finger of the zinc finger protein by: (a) providing a nucleic acid library encoding variants of a zinc finger protein comprising the selected variant first finger, a randomized second finger, and a constant finger that binds to a known subsite; and (b) selecting a second zinc finger protein that binds to a target site comprising the first and second subsites and the known subsite, the second zinc finger protein comprising the selected variant first finger, a selected variant second finger, and the constant finger; and (iv) identifying a third finger of a zinc finger protein by: (a) providing a nucleic acid library encoding variants of a zinc finger protein comprising the selected variant first finger, the selected variant second finger, and a randomized third finger; and (b) selecting a third zinc finger protein that binds to the target site comprising the first, second, and third subsites, the third zinc finger protein comprising the selected variant first finger, the selected variant second finger, and a selected variant third finger, thereby making a zinc finger protein that binds to the target site.

In one embodiment, the first, second, and third fingers are randomized at positions −1, 1, 2, 3, 5, and 6. In another embodiment, the first, second, and third fingers are randomized using degenerate oligonucleotides. In another embodiment, the constant finger is from Zif268, Tramtrack, GLI, or TFIIIA. In another embodiment, a dissociation constant of the zinc finger protein is less than about 0.1 nM. In another embodiment, the steps of selecting the first, second, or third zinc finger protein comprises selecting a pool of variants of the first, second or third zinc finger protein. In one embodiment, the constant fingers are on the N-terminal side of the randomized first finger or the selected variant first finger.

In one embodiment, the nucleic acid library is a phagemid display vector library or a phage display vector library. In another embodiment, the vector phagemid comprises a C-terminal subsequence of the M13 gene III protein.

In one embodiment, the method comprises identifying additional fingers and the target site comprises more than three subsites. In another embodiment, three additional fingers are identified to make a six fingered protein, and the target site comprises six subsites.

In one embodiment, the step of selecting the first, second or third zinc finger protein comprises using a biotinylated target site. In another embodiment, the target site is a TATA box, a p53 binding site or a nuclear receptor element.

In one embodiment, the zinc finger protein is fused to a heterologous DNA binding domain. In another embodiment, the zinc finger protein is fused to a heterologous modular domain involved in protein-protein recognition.

In another embodiment, the method further comprises identifying a heterologous DNA binding domain fused to a zinc finger protein, wherein the heterologous DNA binding domain binds to a secondary target, further comprising the steps of: (a) providing a nucleic acid library encoding variants of a fusion zinc finger protein comprising a randomized heterologous DNA binding domain, and further comprising the first, middle, and last selected variant fingers; and (b) selecting a fourth zinc finger protein that binds to the target site comprising the first, second, and third subsites, wherein the target site further comprises a secondary subsite to which the heterologous DNA binding protein binds, the fourth zinc finger protein comprising the first, second, and third selected variant fingers and a selected variant heterologous DNA binding domain.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1

FIG. 1A depicts the amino acid sequence and secondary structure of the Zif268 zinc fingers (SEQ ID NOS:1–3) (Adapted from Pavletich et al., Science 252:809 (1991)). Randomized positions (circled) correspond to residues −1, 1, 2, 3, 5, and 6 in each of the α helices and include every position that makes a base contact in one of the known zinc finger-DNA complexes (Pavletich et al., Science 252:809 (1991); Fairall et al, Nature 366:483 (1993); Paveltich et al., Science 261:1701 (1993); Elrod-Erickson et al., Structure 4:1171 (1996)). The wild-type Zif268 sequence was retained at all other positions in the new proteins.

FIG. 1B depicts key base contacts (solid arrows) in the Zif268-DNA complex (Pavletich et al., Science 252:809 (1991); Elrod-Erickson et al., Structure 4:1171 (1996)). Most of the bases contacted are located on the primary (guanine-rich) strand (SEQ ID NO:6) (boldface) the complementary strand (SEQ ID NO:7) is shown below the primary strand. Each finger makes several base contacts with its 3 bp subsite (dashed boxes), but also makes important base and phosphate contacts in flanking subsites. The 1.6 Å structure (Elrod-Erickson et al., Structure 4:1171 (1996)) shows that the aspartic acid at position 2 in finger 2 (SEQ ID NO:5) contacts a cytosine that is just outside the canonical 3 bp subsite. Analogous contacts from position 2 in the other fingers (SEQ ID NO:4) (dashed arrows) have less favorable hydrogen-bonding geometry, but binding site selections suggest that these contacts may contribute to recognition (Swimoff et al., Mol Cell. Biol. 15:2275 (1995)). Contacts made by Tramtrack (Fairall et al., Nature 366:483 (1993)) and GLI (Paveltich et al., Science 261:1701 (1993)) also include bases and phosphates outside the canonical 3 bp subsites.

FIG. 1C depicts DNA sequences of the target sites used in the selections. The TATA box is from the adenovirus major late promoter (SEQ ID NO:8) (Ziff et al., Cell 15:1463 (1978)), the p53 binding site is from the human p21$^{WAF1/CIP1}$ promoter (SEQ ID NO:9) (El-Deiry et al., Cell 15:817 (1993); El-Deiry et al., Cancer Res. 55:2910 (1995)), and the NRE is from the human apolipoprotein AI promoter (SEQ ID NO:10) (Ladias et al., Science 251:561 (1991)). One strand of each duplex site is shown.

FIG. 1D depicts the structure of the wild-type Zif268 zinc finger-DNA complex (Pavletich et al., Science 252:809 (1991); Elrod-Erickson et al., Structure 4:1171 (1996)). The DNA is gray, and a ribbon trace of the three zinc fingers is shown in red (finger 1), yellow (finger 2), and purple (finger 3). The 18 residues that were randomized in this study (van der Walls surfaces shown in blue) occupy the major groove of the DNA and span the entire length of the binding site (Image created with Insight II (Biosym Technologies, San Diego, Calif.)).

FIG. 2

FIG. 2 provides an overview of a protocol that successively selects finger 1, finger 2, and finger 3 to create a new zinc finger protein. Fingers that are present in the phage libraries used in these steps are indicated on the left side of each panel. "Zif1" and "Zif2" indicate wild-type Zif268 fingers. R indicates a randomized finger library, and asterisk indicates a selected finger. Small horizontal arrows indicate the multiple cycles of selection and amplification used when selecting each finger by phage display. The right side of each panel shows the binding sites used in selections with the TATA site (SEQ ID NOS:12–17) and indicates the overall binding, mode for the selected fingers (each DNA duplex has biotin (not shown) attached at the 3' end of the upper strand). Vertical arrows indicate how fingers selected in earlier steps are incorporated into the phage libraries used in later steps and reselected to optimize affinity and specificity in the new context.

FIG. 2A: A randomized finger 1 library was cloned into the pZif12 phagemid display vector. Selections with the library were performed in parallel at the TATA, p53, and NRE sites (Rebar et al., Methods Enzymol. 267:129 (1996)).

FIG. 2B: The wild-type Zif1 finger was removed, and a randomized finger 2 cassette was ligated to the appropriate vector pool and optimized by phage display (Rebar et al., Methods Enzymol. 267:129 (1996)).

FIG. 2C: The remaining wild-type finger was removed, and a randomized finger 3 cassette was added and optimized by phage display. To construct the sites used in these selections, the target strand was fused with the higher purine content to the guanine-rich strand of the Zif268 site. Because of the overlapping base contacts that can occur at the junction of neighboring subsites (FIG. 1B), the 3' end of the target site (FIG. 1C) was aligned so that it overlapped with the Zif2 subsite.

FIG. 3

FIG. 3 depicts amino acid sequences of new zinc finger proteins (TATA box, SEQ ID NOS:17 and 18, 19–24, and 25–29; p53 binding site, SEQ ID NOS:30, 31 and 32, and 34 and 35; Nuclear receptor element, SEQ ID NOS:36,37 and 38, and 39–44) that recognize (FIG. 3A) the TATA box (SEQ ID NOS:9 and 45), (FIG. 3B) the p53 binding site (SEQ ID NOS:10 and 46), and (FIG. 3C) the NRE (SEQ ID NOS:11 and 47). A box indicates the clone that was overexpressed and used, for binding studies. Residues that are fully conserved (eight of eight clones) are shown in boldface; residues that are partially conserved (four or more of eight) are denoted by lowercase letters in the consensus sequence below the set of clones (SEQ ID NOS:17, 30, 33, 34 and 38). Each panel indicates how the fingers could dock with a canonical 3 bp spacing (dashed boxes), and dashed arrows indicate plausible base contacts. Recent data from studies of a designed zinc finger protein provide precedence for many of these contacts (Kim et al., *Nature Struct. Biol.* 3:940 (1996)). Detailed modeling suggests many additional contacts, including, some that couple neighboring fingers and subsites.

For the p53 site, there is an alternative, equally plausible, docking arrangement with a 4-bp spacing for one of the fingers. In the alternative arrangement, p53 finger 2 spans a 4-bp subsite (3'-ACAG-5') and finger 3 recognizes the adjacent 3'-GGT-5' subsite. A similar spacing occurs at one point in the GLI-DNA complex (Pavletich & Pabo, *Science* 261:1701 (1993)). A section of the NRE site shows a 5 of 6 bp match (undefined) with the Tramtrack binding site, and these matching segments happen to be aligned such that the new fingers bind in the same register as the Tramtrack fingers (Fairall et al., *Nature* 366, 483 (1993)). Every Tramtrack residue that contacts one of the matching bases (solid arrows) was recovered in the selections. Two residues that do not directly contact the DNA in the Tramtrack complex were also recovered (at positions 5 and 6 in NRE finger 3).

DETAILED DESCRIPTION OF THE INVENTION

I. Introduction

The present invention provides a selection strategy that accommodates the context-dependent interactions between neighboring fingers and subsites in a multi-finger zinc finger protein. This strategy involves gradual assembly of a new zinc finger protein at the desired binding site—adding, and optimizing, one finger at a time while proceeding across the target site.

The protocol includes sequential selection steps, often three selection steps, one for each finger of the new protein (see FIG. 2). A target site comprising, e.g., first, second, and third subsites is selected and a polypeptide display library encoding variants of a zinc finger protein is constructed, where the variants have a first randomized finger and two constant fingers, both either on the N- or C-terminal side of the randomized finger. Fingers to be randomized and constant fingers are selected from known zinc finger proteins. The constant fingers bind to known subsites. In the first step, the target site also comprises two known sites to which the constant fingers bind, as well as first, second, and third subsites. The known subsites are adjacent to the first, second, and third subsites. This target site is used to screen the library for a first zinc finger protein, where the first selected variant finger binds to the first subsite of the target site, and the constant fingers bind to the known sites.

In the next step, a polypeptide display library encoding variants of a zinc finger protein is constructed, where the variants have a first variant finger (selected in the first step), a second randomized finger, and a constant finger. These variants are made by removing one of the constant fingers of the previous step, and adding to the opposite side of the selected variant first finger a randomized second finger. The randomized finger is flanked on one side by the selected variant finger, and on the other side by the constant finger (see FIG. 2B). The library is screened for a second zinc finger protein. The target site for this second step comprises first, second, and third subsites and a single known site that is adjacent to the subsites. The first finger therefore binds to the first subsite of the target site, the second finger binds to the second subsite, and the constant finger binds to the known site.

Finally, a polypeptide display library encoding variants of a zinc finger protein is constructed, where the variants have a first variant finger (selected in the first step), a second variant finger (selected in the second step), and a last randomized finger. These variants are made by removing the constant finger of the previous step, and addition to the opposite site of the second variant finger a third randomized finger. The target site comprising the first, second, and third subsites is used to screen the library for a zinc finger protein, where the fingers bind to the target site.

This method can be used to make zinc finger proteins with any number of fingers, e.g., two, three, four, five, or six or more fingers. To make a zinc finger protein with more than three fingers, the target site is enlarged accordingly to have the appropriate number or subsites, and the step of the selecting the third finger is repeated as often as necessary. For example, for a six finger protein, the last step is repeated three more times. Optionally, more than one variant of a particular finger can be selected during each step, i.e., a pool of variant fingers can be selected at each step. The constant fingers can be present at either the N- or C-terminal side of the first randomized or first selected variant finger, preferably the N-terminal side; the constant fingers are found together on one or the other side (see FIG. 2). The fingers can thus be selected from N- to C- terminus, or from C- to N-terminus.

Optionally, the method can also be used to select a fusion zinc finger protein comprising a variant heterologous DNA binding domain that binds to a secondary target site adjacent to the target site bound by the selected zinc finger protein. The heterologous DNA binding domain is randomized and is fused to a zinc finger protein comprising selected first, second and third variant fingers. The target site additionally comprises a secondary target site. The target site and secondary target site are used to select a fusion protein, where the DNA binding domain binds to the secondary target site, and the zinc finger protein binds to the target site.

In one embodiment, Zif268 is used to provide the fingers to be randomized and the constant fingers of zinc finger protein. Six potential base-contacting positions are randomized in each finger using degenerate oligonucleotides ((Pavletich et al., *Science* 252:809 (1991); Elrod-Erickson et al., *Structure* 4:1171 (1996); see FIG. 1, A and D). FIG. 2 describes this embodiment, as follows: (1) A finger that recognizes the 3' end of the target site is selected by phage display (FIG. 2A). Examples of the technique of phage display have been described in U.S. Pat. No. 5,223,409, U.S. Pat. No. 5,403,484, and U.S. Pat. No. 5,571,698, incorporated herein by reference. At this stage, two wild-type Zif fingers are used as temporary anchors to position the library of randomized fingers over the target site, and a hybrid DNA site was used that has Zif subsites fused to the target site. (2) The selected finger is retained as part of a "growing" protein and, after the distal Zif finger is discarded, phage display is used to select a new finger that recognizes the central region of the target site (FIG. 2B). (3) Finally, the remaining, Zif finger is discarded, and phage display is used to select a third finger that recognizes the 5' region of the target site (FIG. 2C). Optimization of this finger yields the new zinc finger protein.

This strategy ensures that the new fingers are always selected in a relevant structural context. Because of an intact binding site is present at every stage, and because the selections are performed in the context of a growing protein-DNA complex, the present method readily optimizes context-dependent interactions between neighboring fingers and subsites and naturally selects for fingers that will function well together. To ensure that the selected proteins will bind tightly and specifically to the desired target sites, all selections were performed in the presents of calf thymus competitor DNA (3 mg/ml) (Rebar et al., *Methods Enzymol.* 267:129 (1996)). This serves to counterselect against any proteins that bind promiscuously or prefer alternative sites, and the protocol thus directly selects for affinity as well as specificity of binding. Assuming that the calf thymus DNA has one potential binding site per base (that is, binding could conceivably occur in any register on either strand), a 3 mg/ml solution of DNA corresponds to a 0.01 M solution of potential binding, sites. The specific site is present at 40 nM. If the DNA sequence of this competitor were random, each of the $4^9$ (=262.144) possible 9 bp sites would be present, with an average concentration of about 40 nM.

The zinc finger proteins made using the method of the invention have numerous applications, including therapeutic, diagnostic, and research applications such as in cell or animal models and functional genomics. For example, zinc finger proteins can be used to regulate gene expression, allowing for novel human and mammalian therapeutic applications, e.g., treatment of genetic diseases, cancer, fungal, protozoal, bacterial, and viral infection, ischemia, vascular disease, arthritis, immunological disorders, etc., as well as providing means for developing plants with altered phenotypes, including disease resistance, fruit ripening, sugar and oil composition, yield, and color. In addition, the zinc finger proteins of the present invention can be used for diagnostic assays and for functional genomics assays.

As described herein, zinc finger proteins can be designed to recognize any suitable target site for any of the uses described herein, e.g., eukaryotic and prokaryotic genes, cellular genes, viral genes, protozoal genes, fungal genes, and bacterial genes. In general, suitable genes to be regulated include cytokines, lymphokines, growth factors, mitogenic factors, chemotactic factors, onco-active factors, receptors, potassium channels, G-proteins, signal transduction molecules, and other disease-related genes.

A general theme in transcription factor function is that simple binding and sufficient proximity to the promoter are all that is generally needed. Exact positioning relative to the promoter, orientation, and within limits, distance do not matter greatly. This feature allows considerable flexibility in choosing sites for constructing zinc finger proteins. The target site recognized by the zinc finger protein therefore can be any suitable site in the target gene that will allow activation or repression of gene expression by a zinc finger protein, optionally linked to a regulatory domain.

Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region. As described below, typically each finger recognizes 2–4 base pairs, with a two finger zinc finger protein binding to a 4 to 7 bp target site, a three finger zinc finger protein binding to a 6 to 10 base pair site, and a six finger zinc finger protein binding to two adjacent target sites, each target site having from 6–10 base pairs.

II. Definitions

As used herein, the following terms have the meanings ascribed to them unless specified otherwise.

The term "zinc finger protein" or "ZFP" refers to a protein having DNA binding domains that are stabilized by zinc. The individual DNA binding domains are typically referred to as "fingers" A zinc finger protein has least one finger, typically two fingers, three fingers, or six fingers. Each finger binds from two to four base pairs of DNA, typically three or four base pairs of DNA (the "subsite"). A zinc finger protein binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys-$(X)_{2-4}$-Cys-$(X)_{12}$-His-$(X)_{3-5}$-His (SEQ ID NO:60) (where X is any amino acid). Studies have demonstrated that a single zinc finger of this class consists of an alpha helix containing the two invariant histidine residues co-ordinated with zinc along with the two cysteine residues of a single beta turn (see, e.g., Berg & Shi, *Science* 271:1081–1085 (1996)).

A "target site" is the nucleic acid sequence recognized by a zinc finger protein. A single target site typically has about four to about ten base pairs. Typically, a two-fingered zinc finger protein recognizes a four to seven base pair target site, a three-fingered zinc finger protein recognizes a six to ten base pair target site, and a six fingered zinc finger protein recognizes two adjacent nine to ten base pair target sites.

A "subsite" is a subsequence of the target site, and corresponds to a portion of the target site recognized by a single finger, e.g., a 2–4 base subsite, typically a 3 base subsite. A target site comprises at least two, typically three, four, five, six or more subsites, one for each finger of the protein. In addition, the target site can contain "secondary subsites" that are recognized by heterologous DNA binding proteins.

The term "adjacent target sites" refers to non-overlapping target sites that are separated by zero to about 5 base pairs. "$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<$K_d$), as measured using a given assay system (see, e.g., U.S. Pat. No. 5,789,538). The assay system used to measure the $K_d$ should be chosen so that it gives the most accurate measure of the actual $K_d$ of the zinc finger protein. Any assay system can be used, as long is it gives an accurate measurement of the actual $K_d$ of the zinc finger protein. In one embodiment, the $K^d$ for the zinc finger proteins of the invention is measured using an electrophoretic mobility shift assay ("EMSA"), as described in Example 3. Unless an adjustment is made for zinc finger protein purity or activity, the $K_d$ calculations made using the method of Example 3 may result in an underestimate of the true $K_d$ of a given zinc finger protein.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene).

The phrase "RNA polymerase pause site" is described in Uptain et al., *Annu. Rev. Biochem.* 66:117–172 (1997).

"Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., Nature 321:522–525 (1986), and published UK patent application No. 8707252). Backbone sequences for the zinc finger proteins are preferably be selected from existing human $C_2H_2$ zinc finger proteins (e.g., SP-1). Functional domains are preferably selected from existing human genes, (e.g., the activation domain from the p65 subunit of NF-κB). Where possible, the recognition helix sequences will be selected from the thousands of existing zinc finger protein DNA recognition domains provided by sequencing the human genome. As much as possible, domains will be combined as units from the same existing proteins. All of these steps will minimize the introduction of new junctional epitopes in the chimeric zinc finger proteins and render the engineered zinc finger proteins less immunogenic.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

A "heterologous modular domain involved in protein-protein recognition" refers to a protein or a protein domain that has transcriptional modulation activity when tethered to a DNA binding domain, i.e., a zinc finger protein. Typically, a regulatory domain is covalently or non-covalently linked to a zinc finger protein to effect transcription modulation. Such proteins include, e.g., transcription factors and co-factors (e.g., KRAB, MAD, ERD, SID, nuclear factor kappa B subunit p65, early growth response factor 1, and nuclear hormone receptors, VP16, VP64), histone acetyltransferases, histone deacetylases, and transcriptional co-activators and co-repressors (see, e.g., Utley et al., Nature 394:498–502 (1998)).

A "heterologous DNA-binding domain" refers to a DNA binding domain from a protein such as a transcription factor (as described above), e.g., a nuclear hormone receptor or a zinc finger protein.

The term "regulatory domain" refers to both heterologous DNA binding domains and heterologous modular domains involved in protein-protein recognition. "Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide. The nucleotide sequences are displayed herein in the conventional 5'·3' orientation.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. "Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605–2608 (1985); Rossolini et al., Mol. Cell. Probes 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan)

can be modified to yield a functionally identical molecule. Accordingly, each silent variation of a nucleic acid which encodes a polypeptide is implicit in each described sequence.

As to amino acid and nucleic acid sequences, individual substitutions, deletions or additions that alter, add or delete a single amino acid or nucleotide or a small percentage of amino acids or nucleotides in the sequence create a "conservatively modified variant," where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

The following groups each contain amino acids that are conservative substitutions for one another:

1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, *Proteins* (1984) for a discussion of amino acid properties).

III. Polypeptide Display Libraries

The zinc finger proteins of the invention are engineered to recognize a selected target site in the gene of choice. These zinc finger proteins are selected using polypeptide display libraries. The target site is used with the polypeptide display library in an affinity selection step to select variant fingers that bind to the target site. Typically, constant zinc fingers and fingers to be randomized are made from any suitable $C_2H_2$ zinc finger protein, such as SP-1, SP-1C, TFIIIA, GLI, Tramtrack, YY1, or ZIF268 (see, e.g., Jacobs, *EMBO J.* 11:4507 (1992); Desjarlais & Berg, *Proc. Natl. Acad. Sci. U.S.A.* 90:2256–2260 (1993)). The polypeptide display library encoding variants of a zinc finger protein comprising the randomized finger, one or more variants of which will be selected, and, depending on the selection step, one or two constant fingers, is constructed according the methods known to those in the art. Optionally, the library contains restriction sites designed for ease of removing constant fingers, and for adding in randomized fingers. Fingers are randomized, e.g., using degenerate oligonucleotides, mutagenic cassettes, or error prone PCR.

A replicable genetic package means a cell, spore or virus. The replicable genetic package can be eukaryotic or prokaryotic. A polypeptide display library is formed by introducing nucleic acids encoding exogenous polypeptides to be displayed into the genome of the replicable genetic package to form a fusion protein with an endogenous protein that is normally expressed from the outer surface of the replicable genetic package. Expression of the fusion protein, transport to the outer surface and assembly results in display of exogenous polypeptides from the outer surface of the genetic package.

The genetic packages most frequently used for display libraries are bacteriophage, particularly filamentous phage, and especially phage M13, Fd and F1. Most work has inserted libraries encoding polypeptides to be displayed into either gIII or gVIII of these phage forming a fusion protein (see, e.g., WO 91/19818; WO 91/18989; WO 92/01047 (gene III); WO 92/06204; and WO 92/18619 (gene VIII). Such a fusion protein comprises a signal sequence, usually from a secreted protein other than the phage coat protein, a polypeptide to be displayed and either the gene III or gene VIII protein or a fragment thereof. Exogenous coding sequences are often inserted at or near the N-terminus of gene III or gene VIII although other insertion sites are possible. Some filamentous phage vectors have been engineered to produce a second copy of either gene III or gene VIII. In such vectors, exogenous sequences are inserted into only one of the two copies. Expression of the other copy effectively dilutes the proportion of fusion protein incorporated into phage particles and can be advantageous in reducing selection against polypeptides deleterious to phage growth.

In another variation, exogenous polypeptide sequences are cloned into phagemid vectors which encode a phage coat protein and phage packaging sequences but which are not capable of replication. Phagemids are transfected into cells and packaged by infection with helper phage. Use of phagemid system also has the effect of diluting fusion proteins formed from coat protein and displayed polypeptide with wild-type copies of coat protein expressed from the helper phage (see, e.g., WO 92/09690).

Eukaryotic viruses can be used to display polypeptides in an analogous manner. For example, display of human heregulin fused to gp70 of Moloney murine leukemia virus has been reported by Han et al., *Proc. Natl. Acad. Sci. U.SA* 92:9747–9751 (1995). Spores can also be used as replicable genetic packages. In this case, polypeptides are displayed from the outer surface of the spore. For example, spores from *B. subtilis* have been reported to be suitable. Sequences of coat proteins of these spores are provided by Donovan et al., *J. Mol. Biol.* 196:1–10 (1987). Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outer surface proteins are discussed by U.S. Pat. No. 5,571,698, and Georgiou et al., *Nature Biotechnology* 15:29–34 (1997) and references cited therein. Polypeptide display libraries have also been used to make zinc finger proteins (see, e.g., U.S. Pat. No. 5,786,538; Wu et al., *Proc. Natl. Acad. Sci. U.S.A.* 92:344–348 (1995); Jamieson et al., *Biochemistry* 33:5689–5695 (1994); Rebar & Pabo, *Science* 263:671–673 (1994); Choo & Klug, *Proc. Natl. Acad. Sci. U.S.A.* 91:11163–11167 (1994); Choo & Klug, *Proc. Natl. Acad. Sci. U.S.A.* 91: 11168–11172 (1994); Desjarlais & Berg, *Proc. Natl. Acad. Sci. U.S.A.* 90:2256–2260 (1993); Desjarlais & Berg, *Proc. Natl. Acad. Sci. U.S.A.* 89:7345–7349 (1992); Pomerantz et al., *Science* 267:93–96 (1995); Pomerantz et al., *Proc. Natl. Acad. Sci. U.S.A.* 92:9752–9756 (1995); and Liu et al., *Proc. Natl. Acad. Sci. U.S.A.* 94:5525–5530 (1997); Griesman & Pabo, *Science* 275:657–661 (1997); Desjarlais & Berg, *Proc. Natl. Acad. Sci. U.S.A.* 91:11–99–11103 (1994)).

Nucleic acids encoding polypeptides to be displayed by the polypeptide display library are inserted into the genome of a replicable genetic package by standard recombinant DNA techniques (see, e.g., Sambrook et al., *Molecular Cloning, A Laboratory Manual* (2d ed. 1989), incorporated by reference herein). The nucleic acids are ultimately expressed as polypeptides (with or without spacer or framework residues) fused to all or part of the an outer surface protein of the replicable package. Libraries often have sizes of about $10^3$, $10^4$, $10^6$, $10^7$, $10^8$ or more members.

In one embodiment, the framework zinc finger protein is cloned into a phage or phagemid vector as a fusion with, e.g., gene III of filamentous phage, which encodes the coat protein pIII. The zinc finger gene is inserted between segments of gene III encoding the membrane export signal peptide and the remainder of pIII, so that the zinc finger protein is expressed as an amino-terminal fusion with pIII in the mature, processed protein. When using phagemid vectors, the mutagenized zinc finger gene may also be fused to a truncated version of gene III encoding, minimally, the C-terminal region required for assembly of pIII into the phage particle.

The resultant vector library is transformed into *E. coli* and used to produce filamentous phage which express variant zinc finger proteins on their surface as fusions with the coat protein pIII (if a phagemid vector is used, then the this step requires superinfection with helper phage). The phage library is then incubated with target DNA site, and affinity selection methods are used to isolate phage which bind target with high affinity from bulk phage. Optionally, the DNA target is immobilized on a solid support, which is then washed under conditions sufficient to remove all but the phage that bind to the target. Optionally, the DNA target is biotinylated, and streptavidin bound to a solid support is used to isolate bound zinc finger protein and target. After washing, any phage remaining on the support are recovered via elution under conditions which disrupt zinc finger-DNA binding to the target.

Recovered phage are used to infect fresh *E. coli*, which is then amplified and used to produce a new batch of phage particles. The binding and recovery steps are then repeated as many times as is necessary to sufficiently enrich the phage pool for target binders.

IV. Expression and Purification of Zinc Finger Proteins Made Using the Methods of the Invention Nucleic acids encoding zinc finger proteins selected using the methods of the invention can be subcloned and propagated using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

The nucleic acid encoding the zinc finger protein of choice is typically cloned into intermediate vectors for transformation into prokaryotic or eukaryotic cells for replication and/or expression, e.g., for determination of $K_d$. Intermediate vectors are typically prokaryote vectors, e.g., plasmids, or shuttle vectors, or insect vectors, for storage or manipulation of the nucleic acid encoding zinc finger protein or production of protein. The nucleic acid encoding a zinc finger protein is also typically cloned into an expression vector, for administration to a plant cell, animal cell, preferably a mammalian cell or a human cell, fungal cell, bacterial cell, or protozoal cell.

To obtain expression of a cloned gene or nucleic acid, a zinc finger protein is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing the zinc finger protein are available in, e.g., *E. coli*, *Bacillus* sp., and *Salmonella* (Palva et al., *Gene* 22:229–235 (1983)). Kits for such expression systems are commercially available. Eukaryotic expression systems for mammalian cells, yeast, and insect cells are well known in the art and are also commercially available.

The promoter used to direct expression of a zinc finger protein nucleic acid depends on the particular application. For example, a strong constitutive promoter is typically used for expression and purification of zinc finger protein. In contrast, when a zinc finger protein is administered in vivo for gene regulation, either a constitutive or an inducible promoter is used, depending on the particular use of the zinc finger protein. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *Proc. Natl. Acad. Sci. U.S.A.* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 6:757–761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the zinc finger protein, and signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the zinc finger protein, e.g., expression in plants, animals, bacteria, fungus, protozoa, etc. Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the zinc finger protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a zinc finger protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., *J. Biol. Chem..* 264:17619–17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Any suitable method of protein purification known to those of skill in the art can be used to purify zinc finger proteins of the invention (see Ausubel, supra, Sambrook, supra). In addition, any suitable host can be used, e.g., bacterial cells, insect cells, yeast cells, mammalian cells, and the like.

In one embodiment, expression of the zinc finger protein fused to a maltose binding protein (MBP-zinc finger protein) in bacterial strain JM109 allows for straightforward purification through an amylose column (NEB). High expression levels of the zinc finger chimeric protein can be obtained by induction with IPTG since the MBP-zinc finger protein fusion in the pMal-c2 expression plasmid is under the control of the IPTG inducible tac promoter (NEB). Bacteria containing the MBP-zinc finger protein usion plasmids are inoculated in to 2xYT medium containing 10 $\mu$M $ZnCl_2$, 0.02% glucose, plus 50 $\mu$g/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-zinc finger protein proteins are captured on an amylose-bound resin, washed extensively with buffer containing 20 mM Tris-HCl (pH 7.5), 200 mM NaCl, 5 mM DTT and 50 $\mu$M $ZnCl_2$, then eluted with maltose in essentially the same buffer (purification is based on a standard protocol from NEB). Purified proteins are quantitated and stored for biochemical analysis.

The biochemical properties of the purified proteins, e.g., $K_d$, can be characterized by any suitable assay. In one embodiment, $K_d$ is characterized via electrophoretic mobility shift assays ("EMSA") (Buratowski & Chodosh, in *Current Protocols in Molecular Biology* pp. 12.2.1–12.2.7 (Ausubel ed., 1996); see also Example 3).

V. Regulatory Domains

The zinc finger proteins made using the methods of the invention can optionally be associated with regulatory domains for modulation of gene expression. The zinc finger protein can be covalently or non-covalently associated with one or more regulatory domains, alternatively two or more regulatory domains, with the two or more domains being two copies of the same domain, or two different domains.

The regulatory domains can be covalently linked to the zinc finger protein, e.g., via an amino acid linker, as part of a fusion protein. The zinc finger proteins can also be associated with a regulatory domain via a non-covalent dimerization domain, e.g., a leucine zipper, a STAT protein N terminal domain, or an FK506 binding protein (see, e.g., O'Shea, *Science* 254:539 (1991), Barahmand-Pour et al., *Curr. Top. Microbiol. Immunol.* 211:121–128 (1996); Klemm et al., *Annu. Rev. Immunol.* 16:569–592 (1998); Klemm et al., *Annu. Rev. Immunol.* 16:569–592 (1998); Ho et al., *Nature* 382:822–826 (1996); and Pomeranz et al., *Biochem.* 37:965 (1998)). The regulatory domain can be associated with the zinc finger protein at any suitable position, including the C- or N-terminus of the zinc finger protein.

Common regulatory domains for addition to the zinc finger protein made using the methods of the invention include, e.g., heterologous DNA binding domains from transcription factors, effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); and chromatin associated proteins and their modifiers (e.g., kinases, acetylases and deacetylases).

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* 84:825–30 (1996) for a review of proteins and nucleic acid elements involved in transcription; transcription factors in general are reviewed in Barnes & Adcock, *Clin. Exp. Allergy* 25 Suppl. 2:46–9 (1995) and Roeder, *Methods Enzymol.* 273:165–71 (1996)). Databases dedicated to transcription factors are also known (see, e.g., *Science* 269:630 (1995)). Nuclear hormone receptor transcription factors are described in, for example, Rosen et al., *J. Med. Chem.* 38:4855–74 (1995). The C/EBP family of transcription factors are reviewed in Wedel et al., *Immunobiology* 193:171–85 (1995). Coactivators and co-repressors that mediate transcription regulation by nuclear hormone receptors are reviewed in, for example, Meier, *Eur. J. Endocrinol.* 134(2):158–9 (1996); Kaiser et al., *Trends Biochem. Sci.* 21:342–5 (1996); and Utley et al., *Nature* 394:498–502 (1998)). GATA transcription factors, which are involved in regulation of hematopoiesis, are described in, for example, Simon, *Nat. Genet.* 11:9–11 (1995); Weiss et al., *Exp. Hematol.* 23:99–107. TATA box binding protein (TBP) and its associated TAF polypeptides (which include TAF30, TAF55, TAF80, TAF 110, TAF150, and TAF250) are described in Goodrich & Tjian, *Curr. Opin. Cell Biol.* 6:403–9 (1994) and Hurley, *Curr. Opin. Struct. Biol.* 6:69–75 (1996). The STAT family of transcription factors are reviewed in, for example, Barahmand-Pour et al., *Curr. Top. Microbiol. Immunol.* 211:121–8 (1996). Transcription factors involved in disease are reviewed in Aso et al., *J. Clin. Invest.* 97:1561–9 (1996).

In one embodiment, the KRAB repression domain from the human KOX-1 protein is used as a transcriptional repressor (Thiesen et al., *New Biologist* 2:363–374 (1990); Margolin et al., *Proc. Natl Acad. Sci. U.S.A.* 91:4509–4513 (1994); Pengue et al., *Nucl. Acids Res.* 22:2908–2914 (1994); Witzgall et al., *Proc. Natl. Acad. Sci. U.S.A.* 91:4514–4518 (1994)). In another embodiment, KAP-1, a KRAB co-repressor, is used With KRAB (Friedman et al., *Genes Dev.* 10:2067–2078 (1996)). Alternatively, KAP-1 an be used alone with a zinc finger protein. Other preferred transcription factors and transcription factor domains that act as transcriptional repressors include MAD (see, e.g., Sommer et al., *J. Biol. Chem.* 273:6632–6642 (1998); Gupta et al., *Oncogene* 16:1149–1159 (1998); Queva et al., *Oncogene* 16:967–977 (1998); Larsson et al., *Oncogene* 15:737–748 (1997); Laherty et al., *Cell* 89:349–356 (1997); and Cultraro et al., *Mol Cell. Biol.* 17:2353–2359 (19977)); FKHR (forkhead in rhapdosarcoma gene; Ginsberg et al., *Cancer Res.* 15:3542–3546 (1998); Epstein et al., *Mol. Cell. Biol.* 18:4118–4130 (1998)); EGR-1 (early growth response gene product-1; Yan et al., *Proc. Natl. Acad. Sci. U.S.A.* 95:8298–8303 (1998); and Liu et al., *Cancer Gene Ther.* 5:3–28 (1998)); the ets2 repressor factor repressor domain (ERD; Sgouras et al., *EMBO J* 14:4781–4793 ((19095)); and the MAD smSIN3 interaction domain (SID; Ayer et al., *Mol. Cell. Biol.* 16:5772–5781 (1996)).

In one embodiment, the HSV VP16 activation domain is used as a transcriptional activator (see, e.g., Hagmann et al., *J. Virol.* 71:5952–5962 (1997)). Other preferred transcription factors that could supply activation domains include the VP64 activation domain (Seipel et al., *EMBO J* 11:4961–4968 (1996)); nuclear hormone receptors (see, e.g., Torchia et al., *Curr. Opin. Cell. Biol.* 10:373–383 (1998)); the p65 subunit of nuclear factor kappa B (Bitko & Barik, *J. Virol.* 72:5610–5618 (1998) and Doyle & Hunt, *Neuroreport* 8:2937–2942 (1997)); and EGR-1 (early growth response gene product-1; Yan et al., *Proc. Natl. Acad. Sci. U.S.A.* 95:8298–8303 (1998); and Liu et al., *Cancer Gene Ther.* 5:3–28 (1998)).

Kinases, phosphatases, and other proteins that modify polypeptides involved in gene regulation are also useful as regulatory domains for zinc finger proteins. Such modifiers are often involved in switching on or off transcription mediated by, for example, hormones. Kinases involved in transcription regulation are reviewed in Davis, *Mol. Reprod. Dev.* 42:459–67 (1995), Jackson et al., *Adv. Second Messenger Phosphoprotein Res.* 28:279–86 (1993), and Boulikas, *Crit. Rev. Eukaryot. Gene Expr.* 5:1–77 (1995), while phosphatases are reviewed in, for example, Schonthal & Semin, *Cancer Biol.* 6:239–48 (1995). Nuclear tyrosine kinases are described in Wang, *Trends Biochem. Sci.* 19:373–6 (1994).

As described, useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, *Oncogenes*, 2nd ed., The Jones and Bartlett Series in Biology, Boston, Mass., Jones and Bartlett Publishers, 1995. The ets transcription factors are reviewed in Waslylk et al., *Eur. J. Biochem.* 211:7–18 (1993) and Crepieux et al., *Crit. Rev. Oncog.* 5:615–38 (1994). Myc oncogenes are reviewed in, for example, Ryan et al., *Biochem. J.* 314:713–21 (1996). The jun and fos transcription factors are described in, for example, *The Fos and Jun Families of Transcription Factors*, Angel & Herrlich, eds. (1994). The max oncogene is reviewed in Hurlin et al., *Cold Spring Harb. Symp. Quant. Biol.* 59:109–16. The myb gene family is reviewed in Kanei-Ishii et al., *Curr. Top. Microbiol. Immunol.* 211:89–98 (1996). The mos family is reviewed in Yew et al., *Curr. Opin. Genet. Dev.* 3:19–25 (1993).

In another embodiment, histone acetyltransferase is used as a transcriptional activator (see, e.g., Jin & Scotto, *Mol. Cell. Biol.* 18:4377–4384 (1998); Wolffe, *Science* 272:371–372 (1996); Taunton et al., *Science* 272:408–411 (1996); and Hassig et al., *Proc. Natl. Acad. Sci. U.S.A.* 95:3519–3524 (1998)). In another embodiment, histone deacetylase is used as a transcriptional repressor (see, e.g., Jin & Scotto, *Mol. Cell. Biol.* 18:4377–4384 (1998); Syntichaki & Thireos, *J. Biol. Chem.* 273:24414–24419 (1998); Sakaguchi et al., *Genes Dev.* 12:2831–2841 (1998); and Martinez et al., *J. Biol. Chem.* 273:23781–23785 (1998)).

Linker domains between polypeptide domains, e.g., between two zinc finger proteins or between a zinc finger protein and a regulatory domain, can be included. Such linkers are typically polypeptide sequences, such as poly gly sequences of between about 5 and 200 amino acids. Preferred linkers are typically flexible amino acid subsequences which are synthesized as part of a recombinant fusion protein. For example, in one embodiment, the linker DGGGS (SEQ ID NO:48) is used to link two zinc finger proteins. In another embodiment, the flexible linker linking two zinc finger proteins is an amino acid subsequence comprising the sequence TGEKP (SEQ ID NO:49) (see, e.g., Liu et al., *Proc. Natl. Acad. Sci. U.S.A.* 5525–5530 (1997)). In another embodiment, the linker LRQKDGERP (SEQ ID NO:50) is used to link two zinc finger proteins. In another embodiment, the following linkers are used to link two zinc finger proteins: GGRR (SEQ ID NO:51) (Pomerantz et al., 1995, supra), $(G_4S)_n$ (SEQ ID NO:52) (Kim et al., *Proc. Natl. Acad. Sci. U.S.A.* 93, 1156–1160 (1996).); and GGRRGGGS (SEQ ID NO:53); LRQRDGERP (SEQ ID NO:54); LRQKDGGGSERP (SEQ ID NO:55); LRQKD$(G_3S)_2$ERP (SEQ ID NO:56). Alternatively, flexible linkers can be rationally designed using computer program capable of modeling both DNA-binding sites and the peptides themselves (Desjarlais & Berg, *Proc. Natl. Acad. Sci. U.S.A.* 90:2256–2260 (1993), *Proc. Natl. Acad. Sci. U.S.A.* 91:11099–11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Alabama. These linkers optionally have amide linkages, sulfhydryl linkages, or heterofunctional linkages. In addition to covalent linkage of zinc finger proteins to regulatory domains, non-covalent methods can be used to produce molecules with zinc finger proteins associated with regulatory domains.

In addition to regulatory domains, often the zinc finger protein is expressed as a fusion protein such as maltose binding protein ("MBP"), glutathione S transferase (GST), hexahistidine, c-myc, and the FLAG epitope, for ease of purification, monitoring expression, or monitoring cellular and subcellular localization.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Making Nucleic Acid Libraries Encoding Variants of Zinc Finger Proteins

The zinc finger proteins comprising randomized fingers and/or one or two constant regions and/or one or two selected variant fingers were constructed as follows. In the constructs, each cassette encodes one of the Zif268 fingers (FIG. 1A), and randomized codons have A/C/G at the first position, A/C/G/T at the second position, and C/G at the third position. These randomized codons allow 16 side chains at each position (all residues except Cys, Phe, Tyr, and Trp) and they do not give any termination codons. Each cassette encodes a maximum of $16^6 (=1.7 \times 10^7)$ different zinc finger sequences represented by $24^6$ ($=1.9 \times 10^8$) different DNA sequences. All phage display libraries contained between $5.6 \times 10^8$ and $1.9 \times 10^9$ clones. After the finger 1 selections (FIG. 2A), double-stranded DNA was purified from $\geq 10^5$ optimized phagemids, and the first wild-type Zif finger was removed; transformed colonies ($\geq 10^7$) were pooled, and purified DNA from this pool was used to remove the remaining wild-type finger from the selected pool and to construct the finger 3 library. To accommodate the restriction sites used in these cloning steps (Greisman, H. A., thesis, Massachusetts Institute of Technology, Cambridge, Mass. (1997), MIT libraries, Rm 14-0551, Cambridge, Mass. 02139-4307 Indexed in Dissertation Abstracts International Volume 58/04-B, p. 1692 (1997)), residues in the COOH-terminal linker of each randomized finger were changed to TGESR (SEQ ID NO:57) for one round of selections; wild-type residues were restored when the next cassette was added.

Phage display was performed in an anaerobic chamber to ensure proper folding of the zinc fingers (Rebar et al, *Science* 263:671 (1994); Rebar et al., *Methods Enzymol.* 267:129 (1996)). Five to eight cycles of selection and amplification were performed for each finger, and retention efficiencies plateaued at values ranging from ~0.2 to 3% of input phage (Rebar et al, *Methods Enzymol.* 267:129 (1996); Greisman, H. A., thesis, Massachusetts Institute of Technology, Cambridge, Mass. (1997), MIT libraries, Rm 14-0551, Cambridge, Mass. 02139-4307 Indexed in Dissertation Abstracts International Volume 58/04-B, p. 1692 (1997)). Binding, reactions for the p53 finger 3 selections contained the nonbiotinylated duplex competitor 5'-CCCTTGGAACATGTTCCTGATCGCGG-3' (SEQ ID NO:61) (Rebar et al., *Methods Enzymol.* 267:129 (1996)). The p53 target site is pseudosymmetric (FIG. 1C) (El-Deiry et al., *Cell* 15:817 (1993); El-Deiry et al., *Cancer Res.* 55:2910 (1995)), and inadvertent selection of a zinc finger protein that would bind to the opposite strand was to be avoided. The biotinylated sites used in the TATA box selections are shown in FIG. 2, and the sites used for the other selections (Greisman, H. A., thesis, Massachusetts Institute of Technology, Cambridge, Mass. (1997), MIT libraries, Rm 14-0551, Cambridge, Mass. 02139-4307 Indexed in Dissertation Abstracts International Volume 58/04-B, p. 1692 (1997)) were designed in a similar manner; the Zif268 subsites were altered when they were no longer needed (FIG. 2B and C) and any cryptic binding sites that resembled the binding site of interest were removed.

The protocol actually was designed so that a sublibrary of successful zinc finger sequences could be carried over from one selection step (FIG. 2, A or B) to the next. Preliminary sequencing data to analyze the "evolutionary history" of the selections (Greisman, H. A., thesis, Massachusetts Institute of Technology, Cambridge, Mass. (1997), MIT libraries, Rm 14-0551, Cambridge, Mass. 02139-4307 Indexed in Dissertation Abstracts International Volume 58/04-B, p. 1692 (1997)) indicated that a set of finger 1 sequences was carried over into the step in FIG. 2B and that this step then selects for combinations of fingers that work well together.

The pZifl2 phagemid display vector (Rebar et al., *Methods Enzymol.* 267:129 (1996)) encodes a fusion protein that contains (i)Zif268 fingers 1 and 2 (residues 327 to 391 of the intact protein (Christy et al., *Proc. Natl. Acad. Sci. U.S.A.* 85:7857 (1988))); (ii) a linker that introduces an amber codon; and (iii) residues 23 to 424 of the M13 gene III protein. The zinc finger region contains a set of restriction sites that were designed to facilitate the multiple cloning steps in this protocol (Greisman, H. A., thesis, Massachusetts Institute of Technology, Cambridge, Mass. (1997), MIT libraries, Rm 14-0551, Cambridge, Mass. 02139-4307 Indexed in Dissertation Abstracts International Volume 58/04-B, p. 1692 (1997)).

Example 2

Selection with Target Sites

The protocol was tested by performing selections with a TATA box, a p53 binding site, and a nuclear receptor element (NRE) (FIG. 1C). These important regulatory sites were chosen because they normally are recognized by other families of DNA binding proteins and because these sites are quite different from the guanine-rich Zif268 site and from sites that have been successfully targeted in previous design studies (Rebar et al., *Methods Enzymol.* 267:129 (1996)). After the multiple rounds of selections (FIG. 2) were completed, the final phage pools bound tightly to their respective target sites. DNA sequencing of eight clones from each pool revealed marked patterns of conserved residues (FIG. 3), and many of the selected residues (Arg, Asn, Gln, His, and Lys) could readily contribute to base recognition. Each set of proteins exhibits a clear gradient of sequence diversity across the three fingers (FIG. 3), but the finger 1 and finger 2 sequences were more diverse at intermediate stages of the optimization protocol (Rebar et al., *Methods Enzymol.* 267:129 (1996)). For example, after the first step (FIG. 2A), many of the TATA clones had Asn residues at position −1 or position 6 or in both locations. After the selections indicated in FIG. 2B, most clones had Gln at position −1 and Thr at position 6 of finger 1, and these residues also are present in a homologous natural finger that recognizes the same subsite.

Based on the Zif268 (FIG. 1B) and Tramtrack (Fairall et al., *Nature* 366:483 (1993)) structures, the alignments assume that residues at position −1 can contact the 3' base on the primary strand of the subsite, residues at position 3 can contact the central base, and residues at position 6 can contact the 5' base. Guanine bases in the sites appear to prefer Asn at positions −1 and 6, but His or Lys at position 3. Adenine bases appear to prefer Asn at position 3, but prefer Gln at position −1 and, to some extent, at position 6. Several of the subsites recognized by the optimized fingers (FIG. 3) also happen to appear in binding sites for the Tramtrack (Fairall et al., *Nature* 366:483 (1993)) and Gfi-1 zinc finger proteins (Zweidler-McKay et al., *Mol. Cell. Biol.* 16:4024 (1996), incorporated herein by reference), and remarkable similarities were found in the amino acid sequences of the corresponding recognition helices. These homologies include, but are not limited to, the canonical base-contacting residues at positions −1, 3, and 6. For example, finger 4 of the Gfi-1 protein and finger 1 of the NRE proteins appear to recognize the subsite 3'-ACT-5', and the Gfi-1 residues at positions −1, 1, 2, 3, 5, and 6 are QKS DKK (SEQ ID NO:58) (underlined residues match the consensus in the selected fingers). Finger 5 of Gfi-1 and finger 1 of the TATA proteins, appear to recognize the subsite 3'-AAA-5', and the corresponding Gfi-1 residues are QSSNIT (SEQ ID NO:58). (Abbreviations for the amino acid residues are as follows: A, Ala; C, Cys; D, Asp; E, Glu; F, Phe; G, Gfy; H, His; I, Ile; K, Lys; L, Leu; M, Met; N, Asn; P, Pro; Q, Gln; R, Arg; S, Ser; T, Thr; V, Val; W, Trp; and Y, Tyr.)

Example 3

Dissociation Constants of Selected Zinc Finger Proteins

Because of the marked sequence conservation within each of the final phage pools, we used a single clone from each set for further analysis. The corresponding peptides were overexpressed in *Escherichia coli* and purified. Zinc finger regions were subcloned in pET2d (Novagen), and the corresponding, peptides (with end points as in FIG. 1A) were expressed in *E. coli* BL21 (DE3) and purified as described (Rebar et al., *Science* 263:671 (1994)). Affinities of the peptides for their respective target sites were determined by electrophoretic mobility shift analysis.

Dissociation constants were determined essentially as described (Rebar et al., *Science* 263:671 (1994)). However; (i) each $K_d$ was determined in the absence of competitor DNA; (ii) binding buffer contained 15 mM Hepes-NaOH (pH 7.9), 50 mM KCl, 50 mM potassium glutamate, 50 mM potassium acetate, 5 mM $MgCl_2$, 20 µM $ZnSO_4$, acetylated bovine serum albumin (100 µg/ml), 5% (v/v) glycerol, and 0.1% (w/v) NP-40; (iii) binding reactions contained 2 or 4 pM of the labeled site and were equilbrated for 1 hour; (iv) $K_d$ values were calculated from the slopes of Scatchard plots and represent the average of three independent experiments (SD values were all <60%); and (v) mobility shift assays were performed with double-stranded oligonucleotides containing TTT overhangs at the 5'-AGGGGGGCTATAAAAGGGGGT-3' (SEQ ID NO:62) (TATA box)
5'-GCTGTTGGGACATGTTCGTGA-3' (SEQ ID NO:63) (p53 site)
5'-GCCGTCAAGGGTTCAGTGGGG-3' (SEQ ID NO:64) (NRE site)
and 5'-CCAGTAGCGGGGGCGTCCTCG-3' (SEQ ID NO:65) (Zif268 site).

The measured dissociation constants ($K_d$s) were 0.12 nM for the TATA box, 0.11 nM for the p53 binding site, and 0.038 nM for the NRE. These new complexes are almost as stable as the wild-type Zif268-DNA complex ($K_d$ of 0.010 nM under these buffer conditions). Apparent $K_d$s for nonspecific DNA were estimated by competition experiments with calf thymus DNA.

For competition experiments, 8 pM of labeled specific oligonucleotide was mixed with binding buffer containing successive twofold dilutions of calf thymus competitor DNA. An equal volume of binding buffer that contained a fixed amount of protein (sufficient for a 50 to 80% mobility shift in the absence of competitor DNA) was added, after which the reaction mixtures were incubated for ≥1 hour and then subjected to gel electrophoresis (Rebar et al., *Science* 263:671 (1994)). $K_d^{ns}$ (in µg/ml) was calculated from the slope of a $C_t\theta$ versus plot, using the equation:

$$C_t\theta=[-K_d^{ns}/[1-\theta_0]]\theta+[K_d^{ns}/[(1-\theta_0)/\theta_0]]$$

where θ is the fraction of specific site bound by protein in the presence of competitor DNA (at concentration $C_1$), and $\theta_0$ is the fraction bound in the absence of competitor. This equation was derived from equation 3 of Lin & Riggs (*J. Mol. Biol.* 72:671 (1972), incorporated herein by reference). Each $K_d^{ns}$ value represents the average of six plots (three plots in two independent experiments). All SD values were <25%. When calculating $K_d^{ns}/K_d$, it was assumed that each base in the calf thymus DNA represents the beginning of a potential binding site. A simple estimate for the specificity of these new zinc finger proteins can be made by taking various powers of $4^n$ and comparing these numbers with the measured specificity ratios. All of the new proteins have specificity ratios that lie between $4^7$ (=16.384) and $4^8$ (=65.536). This indicates that the proteins like Zif268 itself can effectively specify 7 to 8 bp in the target DNA sites.

Ratios of the nonspecific to specific dissociation constants ($K_d^{ns}/K_d$) indicate that the peptides selected for the TATA box, p53 binding site, and NRE discriminate effectively against nonspecific DNA (preferring their specific sites by factors of 25,000, 54,000, and 36,000, respectively). These ratios are similar to the specificity ratio of 31,000 that were measured for wild-type Zif268. Taken together, the affinities and specificities of the new proteins indicate that they bind as well as many natural DNA-binding proteins.

Example 4

Modeling of the New Zinc Finger Proteins

FIG. 3 depicts amino acid sequences of new zinc finger proteins that recognize (A) the TATA box, (B) the p53 binding site, and (C) the NRE. Residues selected at each of the six randomized positions are shown. Four of the eight p53 clones had a conservative Ser→Thr mutation at position −2 in finger 2; in all other clones, residues outside the randomized regions were identical to those in wild-type Zif268. Six or more of the eight clones in each phage pool encode unique zinc finger proteins. Modeling suggests that these new zinc finger proteins (including those that recognize the TATA box) can bind to B-form DNA.

Many discussions of zinc finger-DNA recognition have considered the idea of a "code" that specifies which positions along the a helix contact the DNA and which side chain-base interactions are most favorable at each position (Choo et al., *Proc. Natl. Acad. Sci. U.S.A.* 91:11163 (1994); Choo etal., *Proc. Natl. Acad. Sci. U.S.A.* 91:11168; Berg *Proc. Natl. Acad. Sci. U.S.A.* 89:11109 (1992); Kievit *Science* 253:1367 (1991); Suzuki et al., *Nucleic Acids Res.* 22:3397 (1994)). There are recurring patterns of contacts in some zinc finger proteins (Pavletich et al., *Science* 252:809 (1991); Fairall et al., *Nature* 366:483 (1993)), and similar patterns are apparent in the proteins that were selected (FIG. 3). Thus, when adenine or guanine occurs in the prim strand of one of the binding sites (the strand corresponding to the guanine-rich strand of the Zif268 site), there often is a conserved residue at position −1, 3, or 6 of the α helix that could form hydrogen bonds with this base. Related patterns have been discussed in previous design and selection studies (Nardelli et al., *Nucleic Acids Res.* 20:4137 (1992); Thukral et al., *Mol. Cell. Biol.* 12:2784 (1992); Desjarlais et al., *Proteins* 12:101 (1992); Desjarlais et al., *Proteins* 13:272 (1992); *Proc. Natl. Acad. Sci. U.S.A.* 89:7345 (1992); *Proc. Natl Acad. Sci. U.S.A.* 91:11099 (1994); Rebar et al., *Science* 263:671 (1994); Choo et al., *Proc. Natl. Acad. Sci. U.S.A.* 91:11163 (1994); Choo et al., *Proc. Natl. Acad. Sci. U.S.A.* 91:11168; Jamieson. et al., *Biochemistry* 33:5689 (1994); Wu et al., *Proc Natl. Acad. Sci. U.S.A.* 92:344 (1995)). There also are strong "homologies" between the zinc fingers we have selected and natural zinc fingers that may recognize the same subsites (FIG. 3).

Such simple patterns are not seen at other positions in the selected proteins. Thus, no simple patterns were found of residues at positions 1, 2, and 5 of the α helix, and when thymine or cytosine occurs on the primary strand (FIG. 3), no simple pattern was found of potential contacts from residues at positions −1, 3, and 6. However, there still are numerous instances in which residues at these positions are highly conserved within a particular set of proteins (FIG. 3), and it is likely that many of these considered residues make energetically significant contributions to folding or binding.

Given the remarkable homology with Tramtrack (FIG. 3), it seems plausible that the Ser and Asp residues at position 2 in NRE fingers 2 and 3 may make the same contacts that corresponding residues make in Tramtrack fingers 1 and 2 (Fairall et al., *Nature* 366:483 (1993)). It is also anticipated that the Lys at position 1 in finger 1 of the TATA box proteins may make a phosphate contact analogous to the contact made by Tramtrack finger 2.

Because no readily predicted pattern of coded contacts is apparent, it is surmised that residues at these positions may be involved in more subtle, context dependent interactions. There are several examples of zinc fingers that have appropriate residues (Arg, His, Asn, or Gln) at positions 1, 3, and 6, but do not make the expected coded contacts with their 3-bp subsites. Examples include some natural fingers, such as finger 3 of GLI (Paveltich et al., *Science* 261:1701 (1993)) and finger 2 of ADR1 (Taylor et al., *Biochemistry* 34:3222 (1995); Cheng et al., *J. Mol. Biol.* 251:1 (1995)), as well as synthetic fingers designed to recognize particular subsites (Nardelli et al., *Nucleic Acids Res.* 20:4137 (1992); Thukral et al., *Mol. Cell. Biol.* 12:2784 (1992); Desjarlais et al., *Proteins* 12:101 (1992); Desjarlais et al., *Proteins* 13 272 (1992); *Proc. Natl. Acad. Sci. U.S.A.* 89:7345 (1992); *Proc. Natl. Acad. Sci. U.S.A.* 91:11099 (1994)). As noted by others (Nardelli et al, *Nucleic Acids Res.* 20:4137 (1992); Thukral et al., *Mol. Cell. Biol.* 12:2784 (1992); Desjarlais et al., *Proteins* 12:101 (1992); Desjarlais et al., *Proteins* 13 272 (1992); *Proc. Natl. Acad. Sci. U.S.A.* 89:7345 (1992); *Proc. Natl. Acad. Sci. U.S.A.* 91:11099 (1994); Taylor et al., *Biochemistry* 34:3222 (1995); Cheng et al., *J. Mol Biol.* 251:1 (1995)), context-dependent interactions may explain these effects.

This sequential selection strategy should provide valuable information about potential patterns in zinc finger-DNA recognition, because it (i) makes few assumptions about the preferred spacing, docking, or contacts of the individual fingers; (ii) yields proteins with essentially wild-type affinities and specificities; (iii) yields sequences that match very will with those of natural zinc finger proteins that recognize similar subsites; and (iv) can readily be adapted to pursue analogous studies with other TFIIIA-like zinc finger proteins.

The sequential selection strategy provides a general and effective method for design of new zinc finger proteins, and this success with a diverse set of target sites suggests that it should be possible to select zinc finger proteins for many important regulatory sequences. These proteins could then be fused with appropriate regulatory of effector domains for a variety of applications. The protocol also could be adapted to allow selection of proteins with four, five, or six fingers or to allow optimization of zinc fingers fused to other DNA binding domains (Pomerantz et al., *Science* 267:93 (1995)). Related selection methods might be developed for other families of multidomain proteins, including other DNA and RNA-binding proteins, and possibly even modular domains involved in protein-protein recognition.

SEQUENCE LISTING

```
<160> NUMBER OF SEQ ID NOS: 65

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence:Zif268 zinc
      finger 1

<400> SEQUENCE: 1

Met Glu Arg Pro Tyr Ala Cys Pro Val Glu Ser Cys Asp Arg Arg Phe
  1               5                  10                  15

Ser Arg Ser Asp Glu Leu Thr Arg His Ile Arg Ile His Thr Gly Gln
             20                  25                  30

Lys

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence:Zif268 zinc
      finger 2

<400> SEQUENCE: 2

Pro Phe Gln Cys Arg Ile Cys Met Arg Asn Phe Ser Arg Ser Asp His
```

```
            1               5              10              15
Leu Thr Thr His Ile Arg Thr His Thr Gly Glu Lys
                 20              25
```

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence:Zif268 zinc
      finger 3

<400> SEQUENCE: 3

```
Pro Phe Ala Cys Asp Ile Cys Gly Arg Lys Phe Ala Arg Ser Asp Glu
  1               5                  10                  15

Arg Lys Arg His Thr Lys Ile His Leu Arg Gln Lys Asp
                 20                  25
```

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:Zif268 zinc
      finger 1 and 3 residues -1, 1, 2 and 3 in the
      alpha helix region

<400> SEQUENCE: 4

```
Arg Ser Asp Glu
  1
```

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:Zif268 zinc
      finger 2 residues -1, 1, 2 and 3 in the alpha
      helix region

<400> SEQUENCE: 5

```
Arg Ser Asp His
  1
```

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:primary
      (guanine-rich) strand in Zif268-DNA complex

<400> SEQUENCE: 6
gcgtgggcgt                                                        10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence:complement
      to primary (guanine-rich) strand in Zif268-DNA
      complex

<400> SEQUENCE: 7
acgcccacgc                                                        10

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence:TATA box
      target site from adenovirus major late promoter

<400> SEQUENCE: 8
ggctataaaa g                                                        11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence:p53 binding
      site target site from human WAF1/CIP1-p21 promoter

<400> SEQUENCE: 9
tgggacatgt t                                                        11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence:nuclear
      receptor element (NRE) target site from human
      apolipoprotein AI promoter

<400> SEQUENCE: 10
caagggttca g                                                        11

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:primary
      strand TATA site binding site used in selection of zinc
      finger 1

<400> SEQUENCE: 11
gcggctataa aagggcgta ctcatcgacg                                     30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:complement
      to primary strand TATA site binding site used in
      selection of zinc finger 1

<400> SEQUENCE: 12
cgtcgatgag tacgcccctt ttatagccgc                                    30

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:primary
      strand TATA site binding site used in selection of zinc
      finger 2

<400> SEQUENCE: 13

```
cggctataaa aggggccgat cgtctg                                        26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:complement
      to primary strand TATA site binding site used in
      selection of zinc finger 2

<400> SEQUENCE: 14
cagacgatcg gccccttta tagccg                                         26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:primary
      strand TATA site binding site used in selection of zinc
      finger 3

<400> SEQUENCE: 15
ccggggctat aaaagtcagt cgtctg                                        26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:complement
      to primary strand TATA site binding site used in
      selection of zinc finger 3

<400> SEQUENCE: 16
cagacgactg acttttatag ccccgg                                        26

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 1 that recognizes TATA box

<400> SEQUENCE: 17

Gln Lys Thr Asn
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 1 that recognizes TATA box

<400> SEQUENCE: 18

Gln Lys Asn Asn
  1

<210> SEQ ID NO 19
<211> LENGTH: 4
<212> TYPE: PRT
```

```
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes TATA box

<400> SEQUENCE: 19

Gln Gln Thr Ala
 1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes TATA box

<400> SEQUENCE: 20

Gln His Thr Gly
 1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes TATA box

<400> SEQUENCE: 21

Gln Leu Thr Gly
 1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes TATA box

<400> SEQUENCE: 22

Gln Arg Thr Gly
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes TATA box

<400> SEQUENCE: 23

Gln Gln Ala Ser
 1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
```

```
        of new zinc finger 2 that recognizes TATA box

<400> SEQUENCE: 24

Gln Ala Ala Ser
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 3 that recognizes TATA box

<400> SEQUENCE: 25

Thr Leu Gln Thr
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 3 that recognizes TATA box

<400> SEQUENCE: 26

Thr Leu His Thr
  1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 3 that recognizes TATA box

<400> SEQUENCE: 27

Thr His Ala Thr
  1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 3 that recognizes TATA box

<400> SEQUENCE: 28

Thr Leu Gly Thr
  1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 3 that recognizes TATA box

<400> SEQUENCE: 29
```

Thr Ser Gly Asp
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 1 that recognizes p53 binding
      site

<400> SEQUENCE: 30

Met Ser His His
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes p53 binding
      site

<400> SEQUENCE: 31

Gln Arg Gly Thr
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes p53 binding
      site

<400> SEQUENCE: 32

Gln Gln Gly Thr
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence:consensus
      amino acid residues -1, 1, 2 and 3 in the alpha helix
      region of new zinc finger 2 that recognizes p53
      binding site
<220> FEATURE:
<221> NAME/KEY: MOD_RES
<222> LOCATION: (2)
<223> OTHER INFORMATION: Xaa = Arg or Gln

<400> SEQUENCE: 33

Gln Xaa Gly Thr
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region of new zinc finger 3 that recognizes p53 binding
site

<400> SEQUENCE: 34

Arg Leu His His
 1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 3 that recognizes p53 binding
      site

<400> SEQUENCE: 35

Arg His His His
 1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 1 that recognizes nuclear
      receptor element (NRE)

<400> SEQUENCE: 36

Gln Ser His Asp
 1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes nuclear
      receptor element (NRE)

<400> SEQUENCE: 37

Asp Ser Ser His
 1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of new zinc finger 2 that recognizes nuclear
      receptor element (NRE)

<400> SEQUENCE: 38

Asp Ser Ser Lys
 1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence:amino acid

```
              residues -1, 1, 2 and 3 in the alpha helix region
              of new zinc finger 3 that recognizes nuclear
              receptor element (NRE)

<400> SEQUENCE: 39

Arg Leu Asp Gly
  1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence:amino acid
              residues -1, 1, 2 and 3 in the alpha helix region
              of new zinc finger 3 that recognizes nuclear
              receptor element (NRE)

<400> SEQUENCE: 40

Arg Pro Asp Asn
  1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:amino acid
              residues -1, 1, 2 and 3 in the alpha helix region
              of new zinc finger 3 that recognizes nuclear
              receptor element (NRE)

<400> SEQUENCE: 41

Arg Leu Asp Asn
  1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:amino acid
              residues -1, 1, 2 and 3 in the alpha helix region
              of new zinc finger 3 that recognizes nuclear
              receptor element (NRE)

<400> SEQUENCE: 42

Arg Pro Asp Gln
  1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:amino acid
              residues -1, 1, 2 and 3 in the alpha helix region
              of new zinc finger 3 that recognizes nuclear
              receptor element (NRE)

<400> SEQUENCE: 43

Arg Gln Asp Gly
  1

<210> SEQ ID NO 44
<211> LENGTH: 4
<212> TYPE: PRT
<213> ORGANISM: Artificial Sequence
<220> FEATURE:
```

```
<223> OTHER INFORMATION: Description of Artificial Sequence:amino acid
      residues -1, 1, 2 and 3 in the alpha helix region
      of new zinc finger 3 that recognizes nuclear
      receptor element (NRE)

<400> SEQUENCE: 44

Arg Lys Asp Gln
  1

<210> SEQ ID NO 45
<211> LENGTH: 11
<212> TYPE: DNA
<213> ORGANISM: Artificial Sequence
<220> FEATURE:
<223> OTHER INFORMATION: Description of Artificial Sequence:complement
      to TATA box target site from adenovirus major late
      promoter

<400> SEQUENCE: 45
cttttatagc c                                                           11

<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence:complement
      to p53 binding site target site from human
      WAF1/CIP1-p21 promoter

<400> SEQUENCE: 46
aacatgtccc a                                                           11

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence:complement
      to nuclear receptor element (NRE) target site from
      human apolipoprotein AI promoter

<400> SEQUENCE: 47
ctgaaccctt g                                                           11

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 48

Asp Gly Gly Gly Ser
  1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 49

Thr Gly Glu Lys Pro
  1               5
```

```
<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence:linker

<400> SEQUENCE: 50

Leu Arg Gln Lys Asp Gly Glu Arg Pro
 1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence:linker

<400> SEQUENCE: 51

Gly Gly Arg Arg
 1

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 52

Gly Gly Gly Gly Ser
 1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence:linker

<400> SEQUENCE: 53

Gly Gly Arg Arg Gly Gly Gly Ser
 1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence:linker

<400> SEQUENCE: 54

Leu Arg Gln Arg Asp Gly Glu Arg Pro
 1               5

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence:linker

<400> SEQUENCE: 55

Leu Arg Gln Lys Asp Gly Gly Gly Ser Glu Arg Pro
 1               5                  10

<210> SEQ ID NO 56
```

```
<211> LENGTH: 16
<212> TYPE: PRT
<213> ORGANISM: Artificial Sequence
<220> FEATURE:
<223> OTHER INFORMATION: Description of Artificial Sequence:linker

<400> SEQUENCE: 56

Leu Arg Gln Lys Asp Gly Gly Gly Ser Gly Gly Gly Ser Glu Arg Pro
 1               5                  10                  15

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 57

Thr Gly Glu Ser Arg
 1               5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of zinc finger 4 of Gfi-1

<400> SEQUENCE: 58

Gln Lys Ser Asp
 1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence:amino acid
      residues -1, 1, 2 and 3 in the alpha helix region
      of finger 5 of Gfi-1

<400> SEQUENCE: 59

Gln Ser Ser Asn
 1

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence:exemplary
      motif of zinc-chelating DNA-binding subdomain from C2H2
      class of zinc finger proteins
<220> FEATURE:
<221> NAME/KEY: MOD_RES
<222> LOCATION: (2)..(3)
<223> OTHER INFORMATION: Xaa = any amino acid
<220> FEATURE:
<221> NAME/KEY: MOD_RES
<222> LOCATION: (4)..(5)
<223> OTHER INFORMATION: Xaa = any amino acid, may be present or absent
<220> FEATURE:
<221> NAME/KEY: MOD_RES
<222> LOCATION: (7)..(18)
<223> OTHER INFORMATION: Xaa = any amino acid
<220> FEATURE:
<221> NAME/KEY: MOD_RES
<222> LOCATION: (20)..(22)
<223> OTHER INFORMATION: Xaa = any amino acid
```

```
<220> FEATURE:
<221> NAME/KEY: MOD_RES
<222> LOCATION: (23)..(24)
<223> OTHER INFORMATION: Xaa = any amino acid, may be present or absent

<400> SEQUENCE: 60

Cys Xaa Xaa Xaa Xaa Cys Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence:duplex
      competitor for p53 zinc finger 3 binding reactions

<400> SEQUENCE: 61
cccttggaac atgttcctga tcgcgg                                            26

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence:TATA box
      target site

<400> SEQUENCE: 62
aggggggcta taaaggggg t                                                  21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence:p53 binding
      site target site

<400> SEQUENCE: 63
gctgttggga catgttcgtg a                                                 21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence:nuclear
      receptor element (NRE) target site

<400> SEQUENCE: 64
gccgtcaagg gttcagtggg g                                                 21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence:Zif268
      target site

<400> SEQUENCE: 65
ccagtagcgg gggcgtcctc g                                                 21
```

What is claimed is:

1. A method of making, in a context-dependent manner, a non-native zinc finger protein that binds to a selected target site comprising first, second and third target subsites, the method comprising the following steps carried out sequentially:

(i) identifying a first finger of the zinc finger protein by
(a) providing a first nucleic acid library encoding zinc finger proteins, wherein said zinc finger proteins comprise a first constant finger native that binds to a first known subsite, a second constant finger that binds to a second known subsite and a first randomized finger;
(b) expressing the zinc finger proteins encoded by the first nucleic acid library;
(c) providing a first target site comprising the first known subsite, the second known subsite and the selected target site, wherein the first known subsite is adjacent to the second known subsite and the second known subsite is adjacent to the first target subsite, and
(d) selecting a first zinc finger protein comprising the first constant finger, the second constant finger and a first selected finger, wherein the first and second constant fingers bind to the first and second known subsites, respectively, and the first selected finger binds to the first target subsite;

(ii) identifying a second finger of the zinc finger protein by
(a) providing a second nucleic acid library encoding zinc finger proteins, wherein the zinc finger proteins comprise the second constant finger, the first selected finger and a second randomized finger;
(b) expressing the zinc finger proteins encoded by the second nucleic acid library;
(c) providing a second target site comprising the second known subsite and the selected target site, wherein the second known subsite is adjacent to the selected target site; and
(d) selecting a second zinc finger protein comprising the second constant finger, the first selected finger and a second selected finger, wherein the second constant finger binds the second known subsite, the first selected finger binds the first target subsite and the second selected finger binds the second target subsite; and (iii) identifying a third finger of the zinc finger protein by:
(a) providing a third nucleic acid library encoding zinc finger proteins, wherein the zinc finger proteins comprise the first selected finger, the second selected finger and a third randomized finger;
(b) expressing the zinc finger proteins encoded by the third nucleic acid library;
(c) providing a third target site comprising the selected target site, and
(d) selecting a third zinc finger protein comprising the first selected finger that binds to the first target subsite of the selected target site, the second selected finger that binds to the second target subsite of the target site, and a third selected finger that binds to the third target subsite of the selected target site, thereby making, in a context-dependent manner, the zinc finger protein that binds to the selected target site.

2. The method of claim 1, wherein the first and second constant fingers are located on the N-terminal side of the first randomized finger.

3. The method of claim 1, wherein the first, second and third randomized fingers are randomized at positions −1, 1, 2, 3, 5, and 6.

4. The method of claim 1, wherein the first, second and third randomized fingers are randomized using degenerate oligonucleotides.

5. The method of claim 1, wherein the first and second constant fingers are from Zif268, Tramtrack, GLI, or TFIIIA.

6. The method of claim 1, wherein the first, second and third nucleic acid libraries are phagemid display vector libraries or phage display vector libraries.

7. The method of claim 6, wherein the vector phagemid comprises a C-terminal subsequence of the M13 gene III protein.

8. The method of claim 1, further comprising identifying additional fingers to make a zinc finger protein having more than three fingers, wherein the selected target site comprises more than first, second and third target subsites.

9. The method of claim 1, wherein the step of selecting the first, second or third zinc finger protein comprises using a biotinylated target site.

10. The method of claim 1, wherein the selected target site is a TATA box, a p53 binding site or a nuclear receptor element.

11. The method of claim 1, wherein the zinc finger protein that binds to the selected site is fused to a heterologous DNA binding domain.

12. The method of claim 11, further comprising the step of:

(iv) identifying a heterologous DNA binding domain that binds to a target site comprising the first, second and third target subsites and a fourth target subsite, by:
(a) providing a fourth nucleic acid library encoding zinc finger proteins fused to a randomized heterologous DNA binding domain, wherein the zinc finger proteins comprise the first, second and third selected fingers;
(b) expressing the zinc finger proteins encoded by the fourth nucleic acid library;
(c) providing a fourth target site comprising the selected target site and a fourth target subsite adjacent to the third target subsite; and
(d) selecting a fourth zinc finger protein that binds to the target site, wherein a heterologous DNA binding domain binds to the fourth target subsite, the fourth zinc finger protein comprising the first, second, and third selected fingers and the heterologous DNA binding domain.

13. The method of claim 1, wherein the zinc finger protein is fused to a heterologous modular domain involved in protein-protein recognition.

14. The method of claim 1, wherein a dissociation constant of the zinc finger protein is less than about 0.1 nM.

15. The method of claim 1, wherein the steps of selecting the first, second or third zinc finger protein comprise selecting a pool of the first, second or third zinc finger proteins.

* * * * *